United States Patent
Yanuma

(10) Patent No.: US 9,486,607 B2
(45) Date of Patent: Nov. 8, 2016

(54) TREATMENT DEVICE

(75) Inventor: Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 908 days.

(21) Appl. No.: 13/283,780

(22) Filed: Oct. 28, 2011

(65) Prior Publication Data
US 2012/0041308 A1 Feb. 16, 2012

Related U.S. Application Data

(63) Continuation of application No. 11/841,218, filed on Aug. 20, 2007, now Pat. No. 8,066,731.

(51) Int. Cl.
| | | |
|---|---|---|
| A61M 25/00 | (2006.01) | |
| A61M 25/01 | (2006.01) | |
| A61M 25/09 | (2006.01) | |

(52) U.S. Cl.
CPC ......... *A61M 25/0068* (2013.01); *A61M 25/01* (2013.01); *A61M 25/003* (2013.01); *A61M 2025/004* (2013.01); *A61M 2025/0037* (2013.01); *A61M 2025/0081* (2013.01); *A61M 2025/0096* (2013.01); *A61M 2025/09175* (2013.01)

(58) Field of Classification Search
CPC .............. A61M 25/0068; A61M 2025/09008; A61M 2025/0081; A61M 25/01; A61M 2025/0096; A61M 25/0067; A61M 25/003; A61M 2025/09175; A61B 17/32056
USPC ....... 600/585; 604/104, 105; 606/37, 39, 45, 606/46, 47, 113, 114, 159, 167, 170, 191, 606/198
See application file for complete search history.

(56) References Cited

U.S. PATENT DOCUMENTS

| | | | |
|---|---|---|---|
| 2,649,092 A * | 8/1953 | Wallace | 604/105 |
| 3,776,219 A | 12/1973 | Brown | |
| 4,023,559 A | 5/1977 | Gaskell | |
| 5,891,153 A | 4/1999 | Peterson | |
| 6,033,381 A | 3/2000 | Kontos | |

(Continued)

FOREIGN PATENT DOCUMENTS

| | | |
|---|---|---|
| EP | 0 778 042 A2 | 6/1997 |
| JP | 2006-507899 A | 3/2006 |
| WO | WO 2004/050161 A1 | 6/2004 |

OTHER PUBLICATIONS

Extended European Search Report dated Nov. 24, 2008.

(Continued)

*Primary Examiner* — Thomas McEvoy
(74) *Attorney, Agent, or Firm* — Scully, Scott, Murphy & Presser, PC

(57) ABSTRACT

A treatment device is provided including a catheter having a lumen that is opened to a distal end of the catheter; a wire passing through the lumen so that the wire is inserted into or retracted from the lumen; and a piece disposed at a distal end of the wire and having the maximum width when the piece is protruded from the distal end of the catheter is set larger than the diameter of the lumen, wherein the piece body is formed of a deformable material having a broad curved surface shape that distributes concentration of pressure acting on tissues, and when the wire is pulled in toward the catheter, the piece being extended in the axial direction by the lumen and reduced in its outer diameter so as to be pulled into the lumen.

9 Claims, 24 Drawing Sheets

(56) References Cited

U.S. PATENT DOCUMENTS

| | | |
|---|---|---|
| 6,053,932 A | 4/2000 | Daniel et al. |
| 6,179,860 B1* | 1/2001 | Fulton et al. .................. 606/200 |
| 6,238,412 B1* | 5/2001 | Dubrul et al. ................. 606/200 |
| 6,258,086 B1 | 7/2001 | Ashley et al. |
| 2004/0167511 A1* | 8/2004 | Buehlmann et al. ........... 606/45 |

OTHER PUBLICATIONS

U.S. Non-Final Office Action of parent U.S. Appl. No. 11/841,218 dated Jul. 16, 2010.

U.S. Final Office Action of parent U.S. Appl. No. 11/841,218 dated Mar. 8, 2011.

Japanese Office Action dated Aug. 14, 2012 from corresponding Japanese Patent Application No. JP 2008-210902, together with an English language translation.

* cited by examiner

TREATMENT DEVICE

CROSS REFERENCE TO RELATED APPLICATIONS

This application is a Continuation Application of U.S. Ser. No. 11/841,218 filed on Aug. 20, 2007, the entire contents of which are incorporated herein by reference.

BACKGROUND OF THE INVENTION

1. Field of the Invention

The present invention relates to a treatment device that is inserted through a natural orifice of a human into a duct cavity.

2. Description of Related Art

Endoscopic retrograde cholangiopancreatography (ERCP) has been known as a method of diagnosing abnormalities of the pancreas, gallbladder, or bile ducts. In ERCP, a catheter is inserted through the papilla of the duodenum, and then a contrast agent is injected directly through the pancreatic or bile ducts, thereby allowing X-ray images to be acquired.

If the entrance of the papilla is narrow or the lining of the bile duct is curved, it is difficult to insert the catheter into the bile duct. Excessive stabbing of the entrance of the papilla with the catheter may cause a mucous membrane edema, unnecessarily narrowing the entrance. Moreover, when the catheter is thrust into a submucosa through the mucous membrane when stabbing the entrance with the catheter, insertion of the catheter becomes more difficult. When a contrast agent is injected in a state that the catheter is thrust into the submucosa, the contrast agent will be injected into the submucosa so that the mucous membrane is inflated to further obstruct the entrance of the papilla. Moreover, when the edema happens or the contrast agent is injected into the submucosa to obstruct the orifice of a pancreatic duct, draining of pancreatic juice is interrupted, resulting in increasing possibility to develop pancreatitis. As another method, there is a method in which a guidewire having a flexible distal end that is relatively easily bent is protruded by about 2 to 3 mm from the distal end of the catheter to access the bile duct. Since the distal end of the guidewire is flexible but narrow, force is likely to concentrate on a single point and therefore excessive stabbing may cause an edema or the guidewire to be thrust into the submucosa. Thus, in order to prevent pancreatitis, it is necessary to decrease the risk of the edema or the puncturing of the mucous membrane as much as possible.

In the conventional procedures, the distal end portion of the catheter where an opening of the lumen for passing a contrast agent is rounded as much as possible so that the distal end portion of the catheter does not cause the edema or the puncturing of the mucous membrane.

SUMMARY OF THE INVENTION

According to a first aspect of the invention, a treatment device includes a catheter having a lumen that is opened to a distal end of the catheter; a wire passing through the lumen so that the wire is inserted into or retracted from the lumen; and a piece disposed at a distal end of the wire and having a maximum width when the piece is protruded out from the distal end of the catheter is set larger than the diameter of the lumen, wherein the piece is formed of a deformable material having a broad curved surface shape that distributes concentration of pressure acting on tissues, and when the wire is pulled in toward the catheter, the piece being extended in the axial direction by the lumen and reduced in its outer diameter so as to be pulled into the lumen.

According to a second aspect of the invention, a treatment device includes a catheter having a lumen that is opened to a distal end of the catheter; a wire passing through the lumen so that the wire is inserted into or retracted from the lumen; and a piece disposed at a distal end of the wire and formed of a deformable material, wherein the piece body has a curved surface shape that distributes concentration of pressure acting on tissues, and when the piece is protruded out from the distal end of the catheter, a projected area of the piece as seen from the front side in the axial direction of the catheter being set larger than the cross-sectional area in the axial direction of the lumen, while when the wire is pulled in toward the catheter to deform the piece body so as to be pulled into the lumen, the projected area of the piece body as seen from the front side in the axial direction of the catheter being decreased to be smaller than or equal to the cross-sectional area of the lumen.

According to a third aspect of the invention, a treatment device includes a catheter having a lumen that is opened to a distal end of the catheter; a wire passing through the lumen so that the wire is inserted into or retracted from the lumen; and a piece disposed at a distal end of the wire and formed of a deformable material, wherein the piece body has a curved surface shape that distributes concentration of pressure acting on tissues, and when the piece is protruded out from the distal end of the catheter, a width of the piece body in a first direction perpendicular to the axial line of the catheter being set larger than the diameter of the lumen and the width of the piece body in a second direction perpendicular to both the axial line and the first direction being set smaller than the diameter of the lumen, while when the wire is pulled in toward the catheter, the piece body being deformed in a manner to alter the width in the first direction so as to be received into the lumen.

According to a fourth aspect of the invention, a treatment device includes a catheter having a lumen that is opened to a distal end of the catheter; a wire passing through the lumen so that the wire is inserted into or retracted from the lumen; and a piece disposed at a distal end of the wire and formed of a deformable material, wherein the piece body has a curved surface shape that distributes concentration of pressure acting on tissues, a maximum width of the piece body when the piece is protruded out from the distal end of the catheter being set larger than the diameter of the lumen, the cross-sectional area at the maximum width portion of the piece body in a direction perpendicular to the axial line of the catheter being set smaller than the section area of the lumen in a direction perpendicular to the axial line of the lumen, and when the wire is pulled in toward the catheter, the maximum width portion being deformed so that the piece is received into the lumen.

According to a fifth aspect of the invention, a treatment device includes a catheter having a guidewire lumen, a knife lumen, and a liquid supply lumen; a wire passing through the guidewire lumen so that the wire is inserted into or retracted from the guidewire lumen; a piece disposed at a distal end of the wire with the maximum width when the piece is protruded out from a distal opening of the guidewire lumen is set larger than the diameter of the guidewire lumen, the distal piece having a deformable piece body; and a conductive wire passing through the knife lumen, a portion of the conductive wire being exposed from the outer periphery on the distal end side of the catheter.

According to a sixth aspect of the invention, a treatment device includes a catheter having a guidewire lumen and a liquid supply lumen, an opening of the guidewire lumen being disposed on a distal end surface of the catheter, and the distal end of the liquid supply lumen being connected to the guidewire lumen; a wire passing through the guidewire lumen so that the wire is inserted into or retracted from the guidewire lumen; and a piece disposed at a distal end of the wire with the maximum width when the piece is protruded out from a distal opening of the guidewire lumen is set larger than the diameter of the guidewire lumen, the distal piece is formed of a deformable material provided with a slit therein.

DESCRIPTION OF EXEMPLARY EMBODIMENTS

Figure 1:
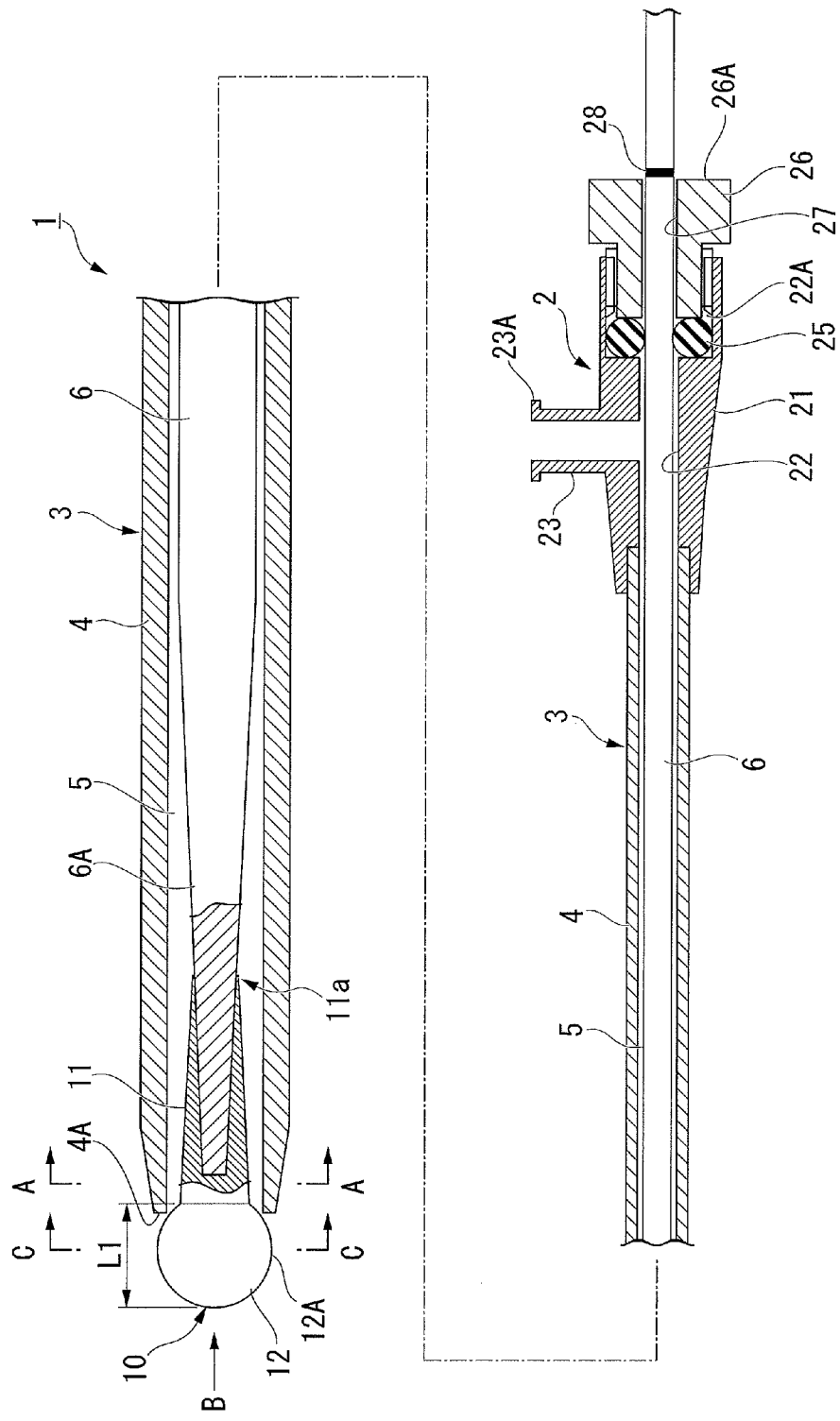
FIG. 1 is a cross-sectional view showing a configuration of a treatment device.

Hereinafter, exemplary embodiments of the present invention will be described. Similar or identical components will be referenced by the same reference numerals throughout the embodiments, and overlapping descriptions will be omitted.

First Embodiment

As shown in FIG. 1, a treatment device 1 has a flexible insertion section 3 extending in a longitudinal direction from an operation section 2 with which an operator operates the treatment device 1.

The insertion section 3 has a catheter 4. A single lumen 5 is formed in the catheter 4 so that a wire 6 can be freely advanced and retreated through the lumen 5. The lumen 5 is a guidewire lumen so in addition to the wire 6, a contrast agent can be injected through the lumen or other guidewires may be inserted through the lumen. If the lumen 5 is used for only the purpose of liquid supply, the lumen 5 only requires a small diameter of about 0.3 mm. To allow passage of guidewires or other treatment tools, a larger lumen diameter is required. The guidewires have various diameter specifications. For example, most typical guidewires have an outer diameter of 0.035 inches (0.89 mm), and a suitable inner diameter of the lumen 5 for these guidewires is in the range of about 0.9 to 1.2 mm. Thinner guidewires have an outer diameter of 0.025 inches (0.64 mm) or 0.018 inches (0.46 mm), and an optimum lumen diameter for these guidewires is in the range of about 0.7 to 0.8 mm or in the range of about 0.5 to 0.6 mm, respectively.

A distal opening of the lumen 5 is formed in a distal end surface 4A of the catheter 4. An outer peripheral portion of the distal end surface 4A of the catheter 4 is cut in a tapered shape with reduced diameter toward the distal end, so as to improve ability to insert the catheter 4 into a duct cavity. The catheter 4 is a tube made of polytetrafluoroethylene (PTFE) or polyethylene resin, for example.

The wire 6 is reduced in diameter toward the distal end, and a distal piece 10 is fitted to an end portion 6A having the smallest diameter by means of adhesive or the like.

The wire 6 may be formed of a metallic wire (stainless steel, NiTi), a plastic solid rod, or a metallic wire covered with a plastic cover. The use of a plastic solid rod or of a metallic wire covered with a plastic cover enables a combined use of the wire 6 and a catheter that uses a high-frequency current, such as a papillotome. The diameter at the portion of the wire 6 inserted through the catheter 4 is smaller than the lumen diameter. For example, if the catheter is compatible with 0.035 inch guidewire and the lumen diameter is 1 mm, the diameter at the portion of the wire 6 is set to about 0.8 mm or smaller.

Figure 2:
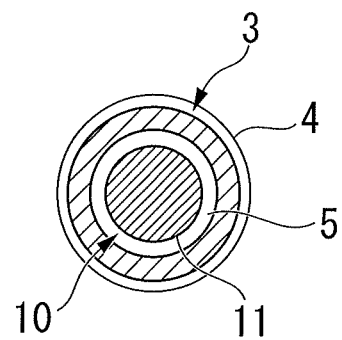
FIG. 2 is a cross-sectional view taken along the line A-A in FIG. 1.

The distal piece 10 is arranged such that a solid spherical piece body 12 is integrally formed with a base portion 11 that covers the outer periphery of the end portion 6A on the distal end side of the wire 6. As shown in FIG. 2, the outer diameters of the base portion 11 and the portion of the wire 6 located closer to the operator side than the base portion 11 are smaller than the diameter of the lumen 5. As shown in FIG. 1, in a state in which the piece body 12 is protruded from the distal end, the maximum outer diameter of the piece body 12 is set larger than the diameter of the lumen 5 and smaller than the outer diameter of the catheter 4. For example, the maximum outer diameter is about 1.2 mm if the lumen diameter is 1 mm. An axial length L1 of the piece body 12 having a substantially spherical shape is equal to or smaller than or equal to twice of the lumen diameter. Since the distal piece 10 has a curved surface shape that distributes concentration of pressure acting on tissues, a distal end portion of the insertion section 3 becomes to assume a rounded shape. Here, the curved surface shape for distributing the concentration of pressure acting on tissues refers to a curved surface shape that has an area larger than that of the distal end of the conventional guidewire or of the distal end of the conventional catheter and has a large curvature (hereinafter such a shape will be referred to as a broad and large-curvature curved surface shape). The length L1 being equal to or smaller than or equal to twice of the lumen diameter is suitable for rounding off the distal end of the insertion section 3 without creating a sharp-edged shape.

Figure 3:
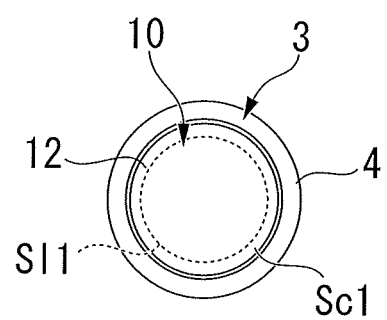
FIG. 3 is a view taken from the arrow B in FIG. 1.
Figure 4:
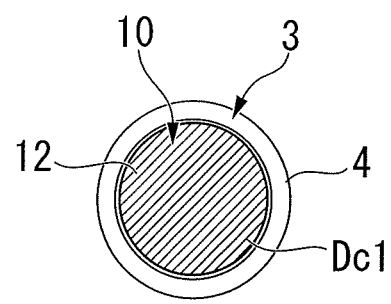
FIG. 4 is a cross-sectional view taken along the line C-C in FIG. 1.

As shown in FIG. 3, a projected area Sc1 of the piece body 12 as seen from the front side in the axial direction of the piece body 12 is set larger than a cross-sectional area S11 of the lumen 5 perpendicular to the axial line of the lumen 5. As shown in FIG. 4, a cross-sectional area Dc1 of the piece body 12 at a portion having a maximum width in a direction perpendicular to the axial line (hereinafter the portion will be referred to as a maximum width portion) is set larger than the cross-sectional area S11 of the lumen 5. Alternatively, the piece body 12 may have a bombshell shape.

The distal piece 10 is formed of a deformable material such as an elastic material. When it is desired to have the piece body 12 have a diameter much larger than the lumen diameter, suitable examples of the elastic material include rubber having a relatively large elasticity (for example, latex rubber, silicone rubber, and urethane rubber) and elastomeric plastic (for example, polyamide elastomer and urethane elastomer). A contrast material such as bismuth oxide, barium sulfate or tungsten may be mixed with the elastic material, allowing X-rays to be taken. In addition, the outer surface of the distal piece 10 is subjected to a lubrication treatment (for example, hydrophilic lubricant coating, water-repelling lubricant coating, teflon coating, and silicone oil coating).

Figure 5:
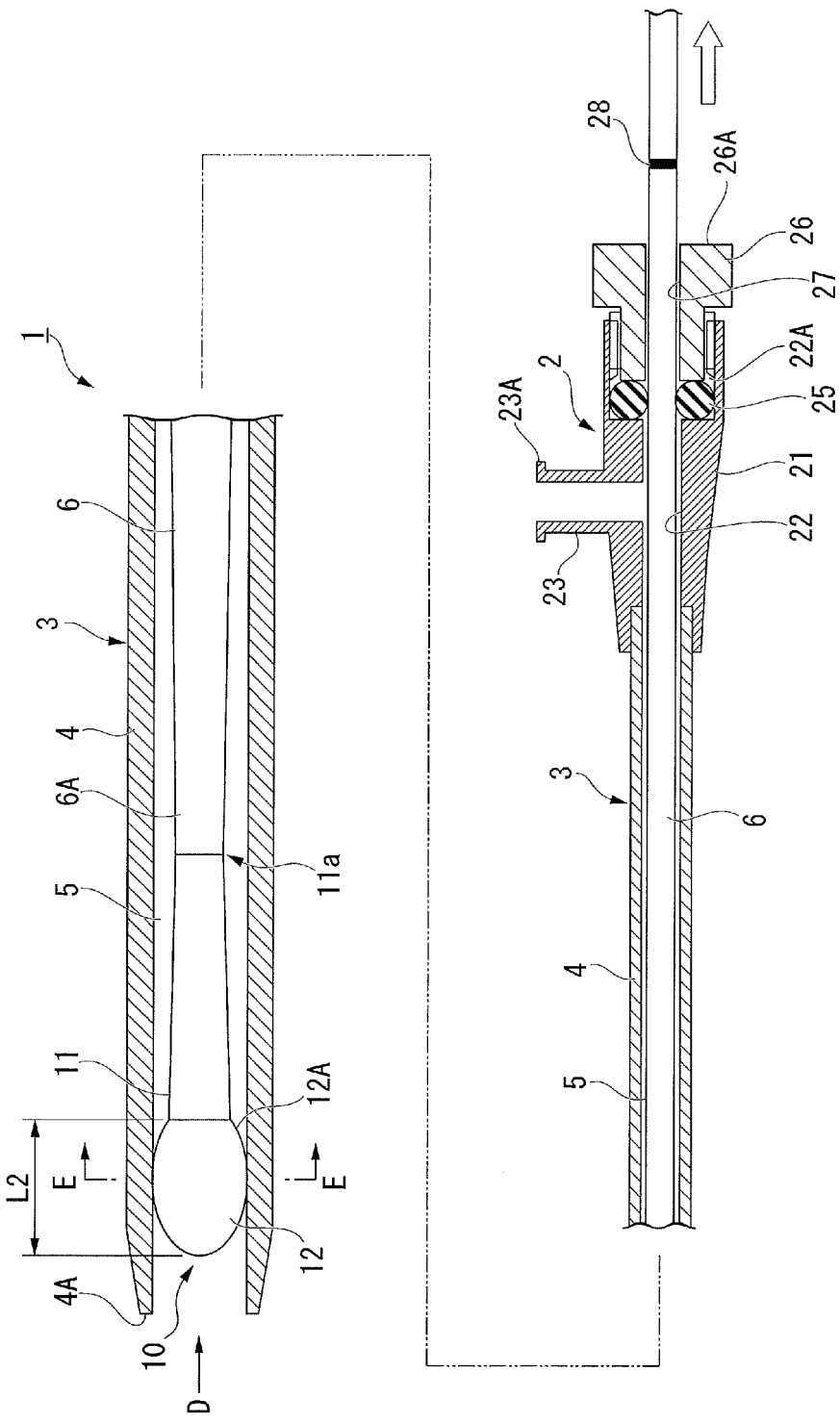
FIG. 5 is a view showing the case in which a distal piece is housed in a lumen.
Figure 6:
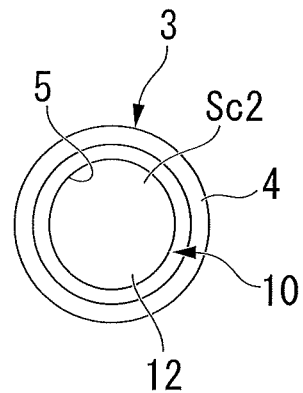
FIG. 6 is a view taken from the arrow D in FIG. 5.
Figure 7:
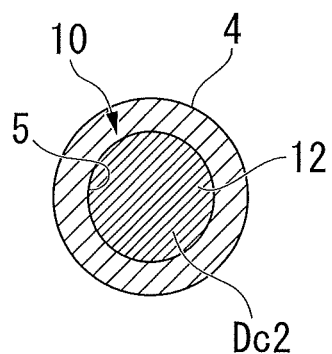
FIG. 7 is a cross-sectional view taken along the line E-E in FIG. 5.

Since the distal piece 10 is formed of an elastic material, the distal piece 10 can be deformed and housed in the catheter 4. When the wire 6 is pulled in toward the catheter 4, the distal piece 10 collides against the distal end surface 4A of the catheter 4 so the distal piece 10 is deformed in a manner to extend in the axial direction. Accordingly, the outer diameter of the piece body 12 is decreased to be smaller than or equal to the lumen diameter and is thus pulled into the lumen 5. As a result, as shown in FIG. 5, the piece body 12 is crushingly reduced in its maximum outer diameter. Also, an axial length L2 becomes larger than the axial length L1. When the piece body 12 is pulled into the lumen 5, as shown in FIG. 6 which is taken from the arrow D in FIG. 5, a projected area (Sc2) of the piece body 12 in the axial direction is also decreased. The projected area Sc2 of the piece body 12 when pulled into the lumen 5 becomes smaller than or equal to the cross-sectional area S11 of the lumen 5. As shown in FIG. 7, the cross-sectional area at the maximum diameter portion of the piece body 12 is decreased when pulled into the lumen 5, and the cross-sectional area Dc2 of the piece body 12 when pulled into the lumen 5 becomes smaller than or equal to the cross-sectional area S11 of the lumen 5. Here, since the distal piece 10 is formed of an elastic material, the distal piece 10 can be restored into substantially the same shape as its original shape when the distal piece 10 protrudes out from the distal end of the catheter 4 after being pulled into the catheter 4.

As shown in FIG. 1, the operation section 2 has an operation body 21 fixed to the proximal end of the catheter 4. The operation body 21 has a hole 22 that is formed therethrough. The hole 22 has a diameter equal to or larger than the diameter of the lumen 5. A liquid supply port 23 is connected to the hole 22. The liquid supply port 23 protrudes from the side portion of the operation body 21 and a connector 23A is formed in the end portion of the liquid supply port 23. A syringe (not shown) storing a contrast agent therein may be connected to the connector 23A.

The wire 6 passes through the hole 22 of the operation body 21. The diameter of an end portion 22A of the hole 22 located closer to the proximal end than the liquid supply port 23 is enlarged. A sealing member 25 is inserted in the end portion 22A and then a handle 26 is screwed thereto. As the sealing member 25, a ring-shaped elastic member such as an O-ring can be used. The sealing member 25 can be compressed and deformed by rotating the handle 26 so that the inner diameter changes between 0 and the lumen diameter or more. The diameter of the handle 26 can be enlarged to a flange shape so an operator can easily grip the handle 26, and a through-hole 27 is disposed concentric to the hole 22 of the operation main body 21. The wire 6 also passes through the through-hole 27. When the handle 26 is rotated in a state that the wire 6 is passed through the sealing member 25, the sealing member 25 is squeezed and thus the position of the wire 6 is fixed. At this time, a liquid-tight seal is formed in a space between the sealing member 25 and the wire 6, preventing liquid supplied from the liquid supply port 23 from leaking toward the operator side. In addition, a mark 28 is provided on the wire 6. When the mark 28 is aligned at a proximal surface 26A of the handle 26, on the distal end side, an inclined surface 12A of the piece body 12 located immediately before the proximal side from the maximum diameter portion is moved to a position where the inclined surface 12A almost collides against a distal opening 5A of the lumen 5 at the distal end surface 4A of the catheter 4.

Next, the procedure of ERCP using the treatment device 1 will be described.

First, an endoscope is inserted through a natural orifice of a patient, a mouth, and is introduced into the duodenum. In this embodiment, a side-view type endoscope may be used having an observation window on a side portion thereof.

While taking images of the interior of the body using an observation device installed in the endoscope, the distal end of the endoscope is advanced in the vicinity of a papilla of a treatment target. The catheter 4 of the treatment device 1 is inserted through a forceps plug of the endoscope disposed close to the operator side into an instrument channel. At this time, the distal piece 10 is in the state shown in FIG. 1: i.e., the distal piece 10 is protruded out so as to almost collide against the distal end surface 4A of the catheter 4. Moreover, the handle 26 is rotated to decrease the inner diameter of the sealing member 25, fixing the position of the wire 6.

Figure 8:
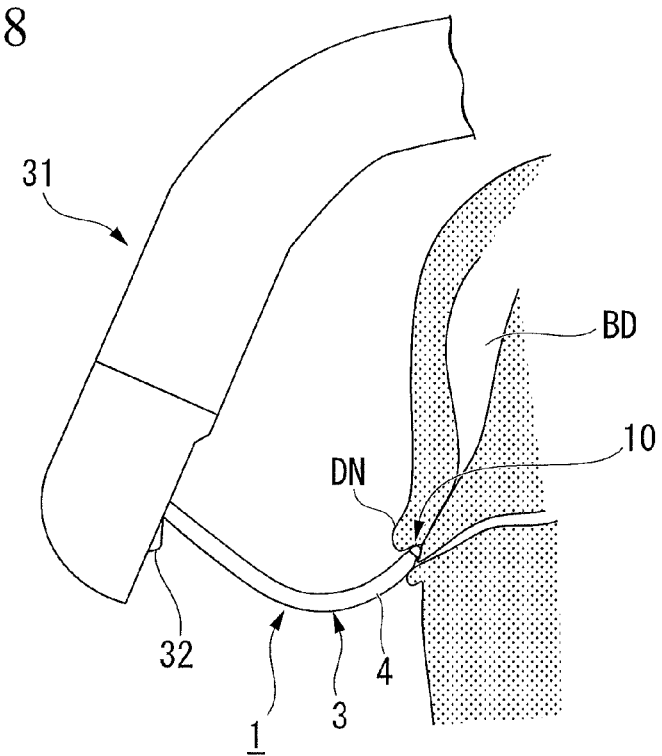
FIG. 8 is a view showing the case in which a distal piece is inserted into a papilla.
Figure 9:
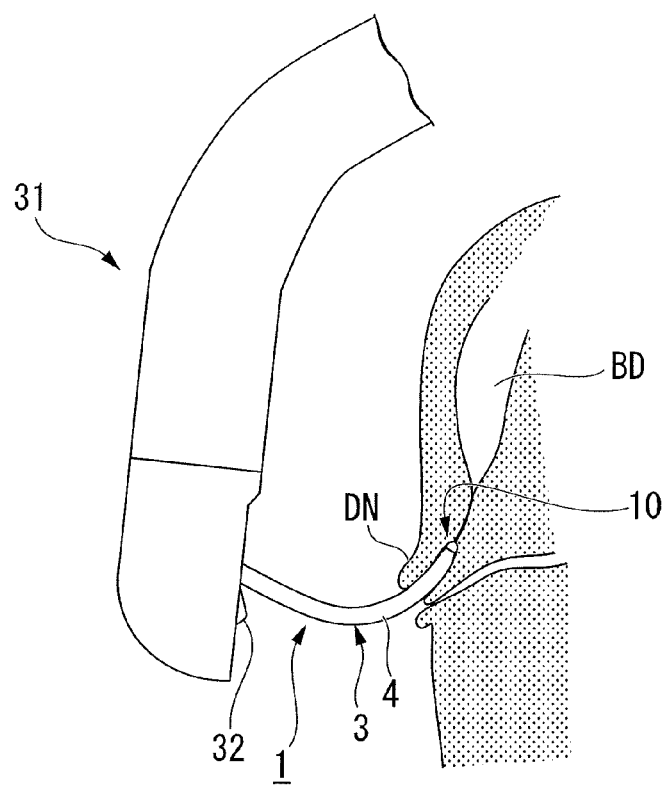
FIG. 9 is a view showing the case in which a distal piece and a distal end portion of a sheath are inserted through a papilla into a bile duct.
Figure 10:
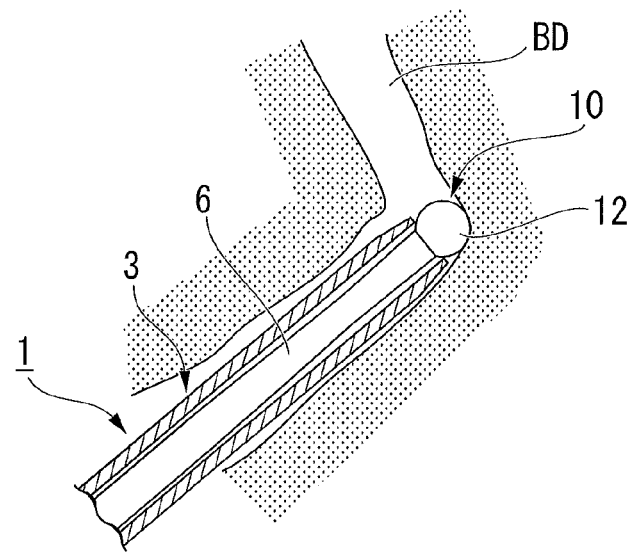
FIG. 10 is a view showing the case in which a catheter is inserted into a curved bile duct.
Figure 11:
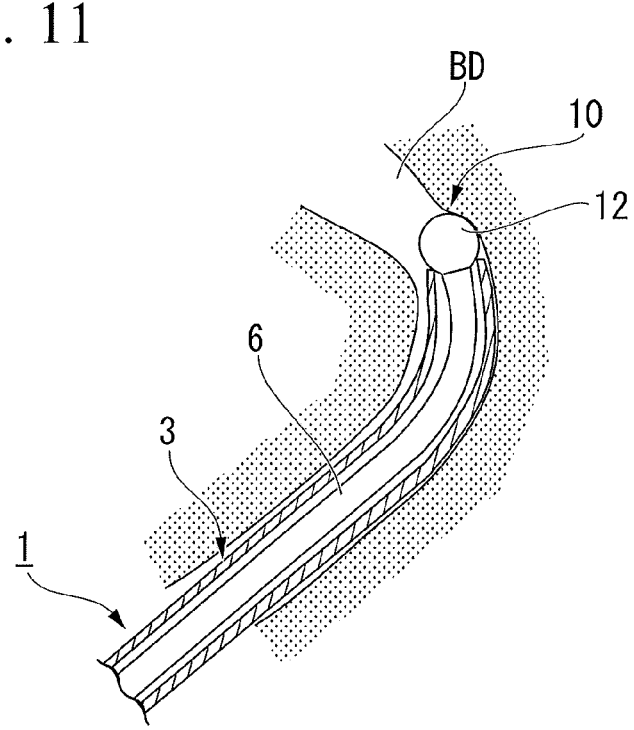
FIG. 11 is a view showing the case in which a catheter and a distal piece are bent and advanced in accordance with the shape of a bile duct.

As shown in FIG. 8, the catheter 4 is protruded out toward a papilla DN by a forceps elevator 32 provided at the distal end of an endoscope 31. With the angle control of the endoscope 31, the control of the forceps elevator 32, and the advancing and retracting of the catheter 4, the distal end of the catheter 4 is inserted into the papilla DN. At this time, since the distal piece 10 has the broad, large-curvature curved surface shape, the force applied thereto at the time of the insertion is distributed. Moreover, since the distal end of the treatment device 1 is generally smooth and rounded, the distal end does not damage or thrust into mucous membranes. As shown in FIG. 9, the distal end of the catheter 4 and the distal piece 10 are inserted through the papilla DN into further inside of a bile duct BD in a smooth manner. Here, as shown in FIG. 10, even if the bile duct BD is greatly curved, since the piece body 12 of the distal piece 10 makes contact with tissues on the spherical surface having the broad, large-curvature curved surface shape, the force applied from the treatment device 1 to the wall of the bile duct BD is not concentrated thereon but distributed over a broad area. For this reason, a small load is applied to the wall of the bile duct BD. When the catheter 4 is pushed further into the bile duct BD, as shown in FIG. 11, the catheter 4 and the wire 6 are deformed, curved and inserted through the bile duct in a manner to assume the shape of the bile duct BD.

Figure 12:
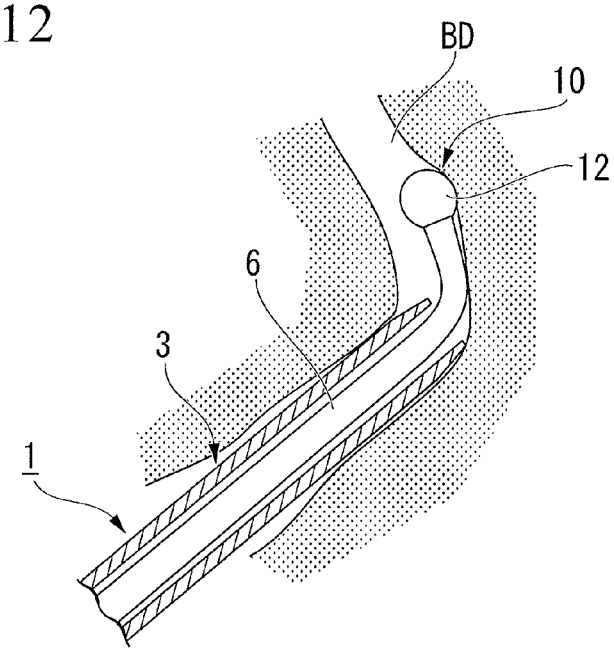
FIG. 12 is a view showing the case in which a distal piece is made to protrude out from a catheter and is bent and advanced in accordance with the shape of a bile duct.
Figure 13:
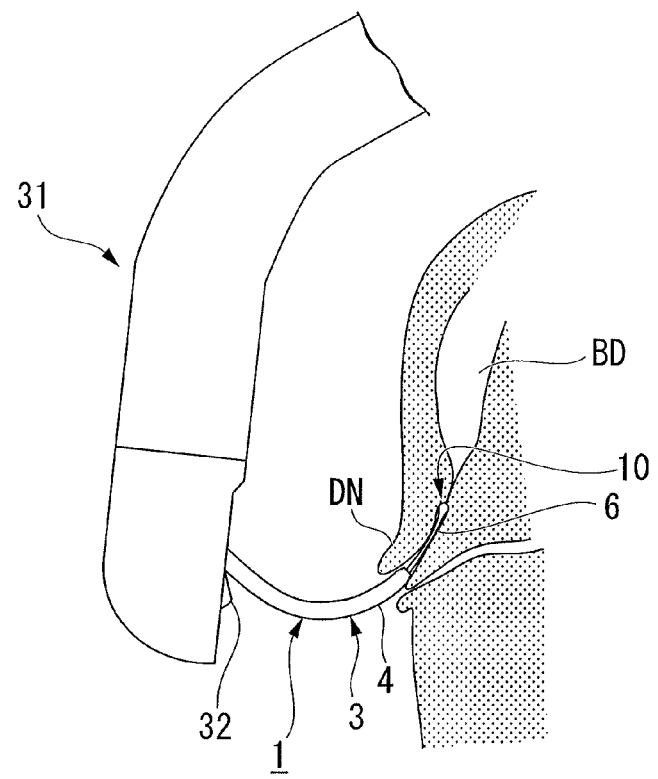
FIG. 13 is a view showing the case in which a distal piece is made to be advanced from a catheter in a manner similar to the case of FIG. 12.
Figure 14:
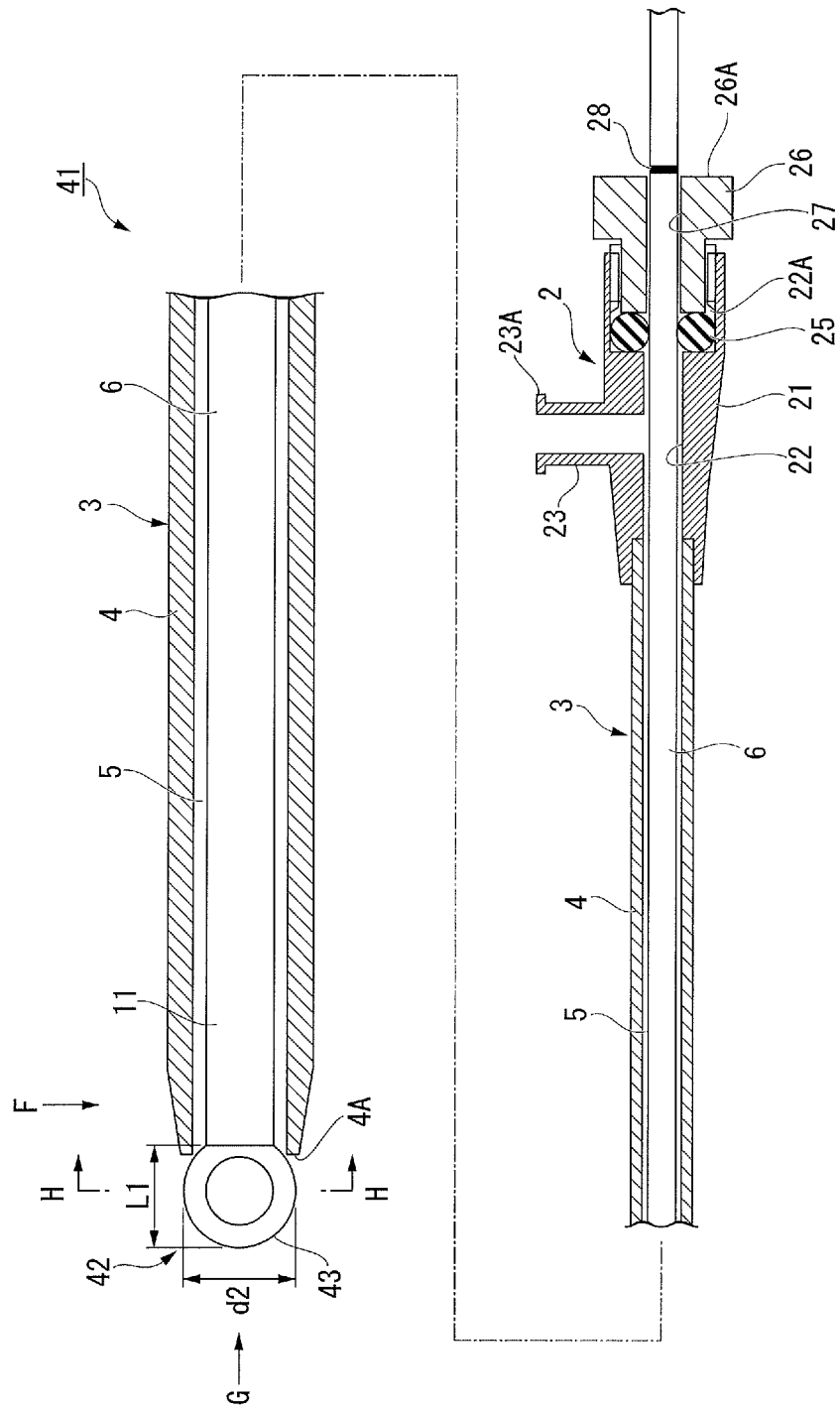
FIG. 14 is a view showing another example of the shape of a distal piece.

As shown in FIG. 12, the catheter 4 may not be inserted at all but only the wire 6 may be pushed into the bile duct BD. In this case, the handle 26 is loosened to push in only the wire 6. Since the distal piece 10 having a sufficiently large spherical shape is provided at the distal end of the wire 6, the wire 6 can be inserted into further inside of the papilla DN in a smooth manner without damaging or thrusting into the mucous membranes. Moreover, since a small-diameter portion 11a is provided to the base portion 11 disposed at the right rear side of the piece body 12, the wire 6 can be more easily curved in a manner to adopt the shape of the bile duct BD. As shown in FIG. 13, when the wire 6 is inserted beyond the papilla DN, the catheter 4 is inserted beyond the papilla along the wire 6.

When the catheter 4 is inserted to a desired position, a contrast agent is injected from a syringe mounted on the liquid supply port 23. The contrast agent is introduced to the distal end along a path between the lumen 5 and the wire 6 and then injected into the bile duct BD through a gap between the distal piece 10 and the catheter 4. With X-ray equipment, clear X-ray images of the bile duct BD can be taken.

Next, the wire 6 is pulled into the lumen 5 of the catheter 4. Here, if the catheter 4 is inserted together with the wire 6, the handle 26 is loosened to pull only the wire 6. Then, the distal piece 10 is deformed in a manner that the diameter becomes smaller than or equal to the lumen diameter and that the distal piece 10 is pulled into the lumen 5. When the wire 6 is pulled further, the wire 6 passes through the catheter 4 and is pulled out from the opening of the operation section 2 disposed closer to the operator side in a state that the distal piece 10 is extended long and reduced in its diameter, projected area, and cross-sectional area. When the wire 6 is pulled out, other guidewires can be inserted according to the purpose of use. Alternatively, by pulling out only the catheter 4 while leaving the wire 6 in the bile duct BD, other treatment tools may be inserted along the wire 6. When necessary treatments using other treatment tools are completed, the wire 6 is pulled out of the bile duct BD.

In this embodiment, since the portion of the distal piece 10 corresponding to the distal end portion of the insertion section 3 is formed in a smooth round shape, it is possible to insert the insertion section 3 beyond the papilla DN in a smooth manner without damaging or thrusting into the mucous membranes. In the conventional procedure, even when the distal end portion of the catheter is rounded, it was difficult to form the distal end of the insertion section in a completely smooth spherical surface shape, due to the presence of the edges of the distal opening of the guidewire insertion lumen. In the conventional art, when using a catheter having a narrow distal end, the distal end of the insertion section becomes a narrow, sharp-edged shape. From this reason and due to the presence of the edges of the lumen, the operation of the conventional tool and decision making by an operator upon using the tool required a great deal of caution. A method may be employed in which a guidewire having a flexible distal end that can be easily curved is protruded by about 2 to 3 mm from the distal end of the catheter to access the bile duct. Though the guidewire is easily curved, since the distal end of the guidewire of the conventional art is narrower than the lumen diameter of the catheter, if a large pressing force is applied thereto, the pressure may be concentrated on a single point, thereby damaging or thrusting into the mucous membranes. Accordingly, the operation required a great deal of caution. In this embodiment, by virtue of the distal piece 10, the edges of the lumen 5 are not directly pressed on tissues, and the distal end portion of the insertion section 3 is formed in a generally broad and rounded shape. Accordingly, the above-described problems are solved or alleviated.

Since the distal piece 10 is configured to be elastically deformable, when the wire 6 is pulled from the operator side, the distal piece 10 is deformed in a manner that the distal piece 10 is pulled into the lumen 5. Therefore, the wire 6 and the distal piece 10 can be pulled out until the proximal side while the catheter 4 is indwelled. Accordingly, it is possible to insert other guidewires according to necessity.

Since the distal piece 10 is subjected to a lubrication treatment, the distal piece 10 is made more difficult to thrust into the mucous membranes. Moreover, the distal piece 10 can easily slide its way to a curved duct cavity. In addition, since the friction between the distal piece 10 and the inner wall of the lumen 5 is reduced, the distal piece 10 can be easily deformed with a small force.

By mixing a contrast agent into the distal piece 10, it is possible to perform the insertion while imaging and observing the movement of the distal piece 10 under X-rays.

The distal piece 10 may be integrally formed with the wire 6.

Second Embodiment

Figure 17:
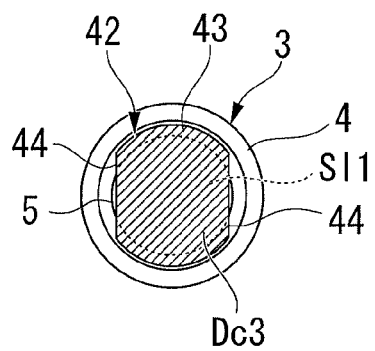
FIG. 17 is a view taken along the line H-H in FIG. 15.

As shown in FIG. 17, in a treatment device 41, the distal piece attached to the distal end of the wire 6 has a shape different from that of the above-described embodiment.

Figure 15:
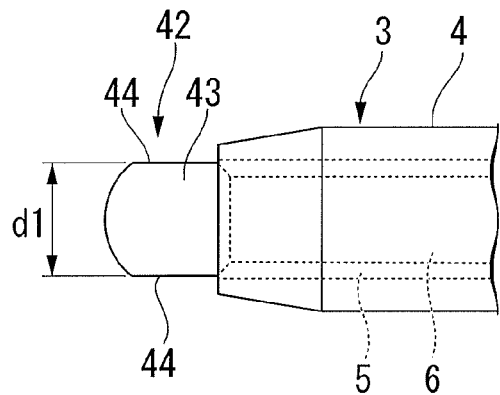
FIG. 15 is a view taken from the arrow F in FIG. 14.
Figure 16:
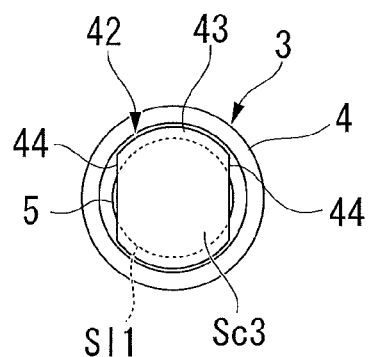
FIG. 16 is a view taken from the arrow G in FIG. 14.

The treatment device 41 is provided with a distal piece 42 having a broad, large-curvature curved surface shape that distributes concentration of pressure acting on tissues, causing the distal end portion of the insertion section 3 to form a generally rounded shape. The distal piece 42 is provided with a piece body 43 configured to protrude out from the distal end surface 4A of the catheter 4, and the piece body 43 has a pair of flat side surfaces 44. The side surfaces 44 are parallel to each other on both lateral portions of a solid spherical body. As shown in FIG. 15, a width d1 between the pair of flat side surfaces 44 is set smaller than the diameter of the lumen 5. A length d2 of the piece body 43 in the vertical direction (first direction) perpendicular to both the horizontal direction (second direction) connecting the pair of side surfaces 44 and the axial direction is set smaller than the outer diameter of the catheter 4. As shown in FIG. 16, a projected area Sc3 in the axial direction of the piece body 43 is set larger than the cross-sectional area S11 of the lumen 5. In addition, as shown in FIG. 17, the cross-sectional area Dc3 of the piece body 43 at the maximum width portion having a maximum width in the vertical direction is set larger than the cross-sectional area S11 of the lumen 5.

Figure 18:
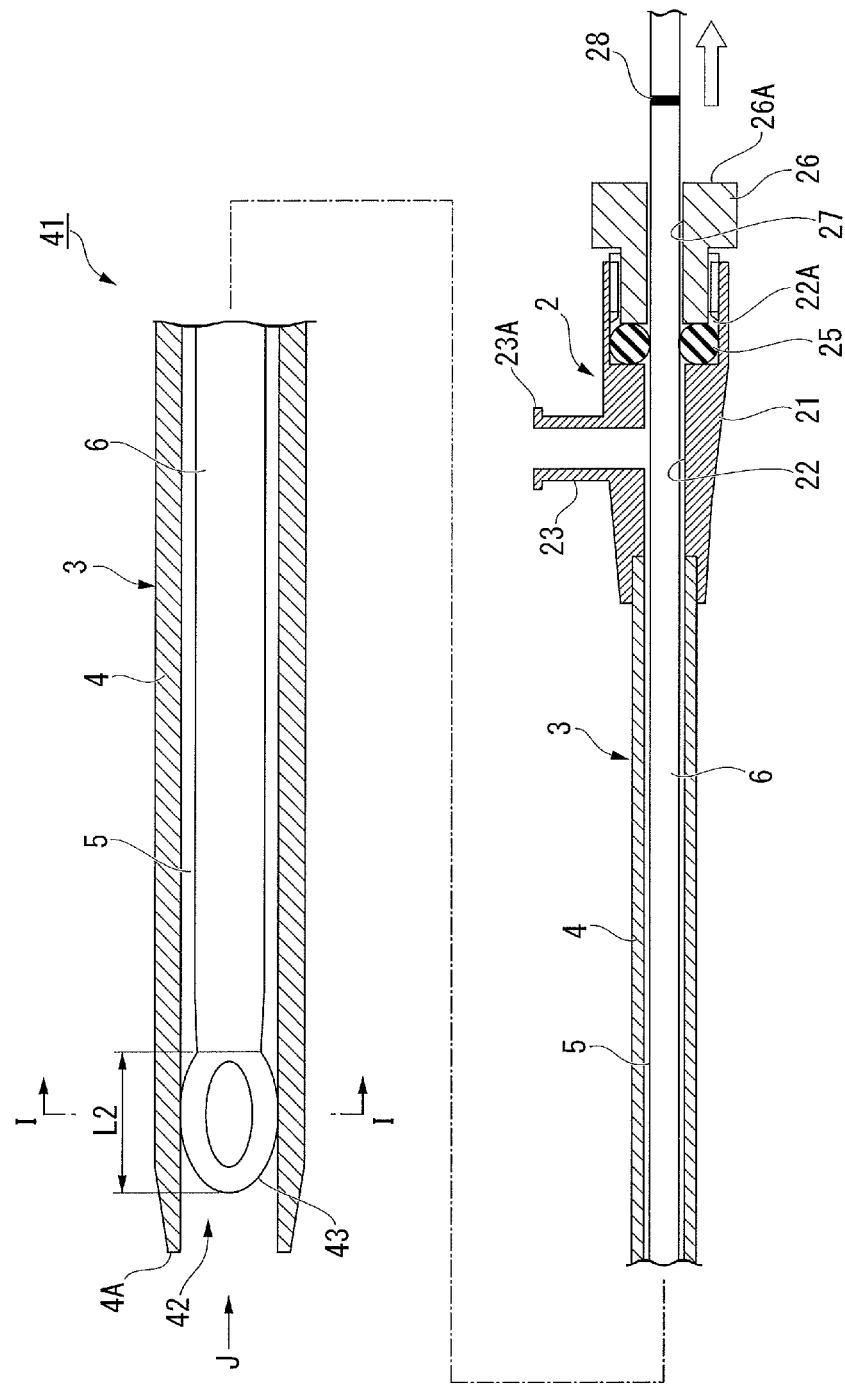
FIG. 18 is a view showing the case in which a distal piece is housed in a lumen.
Figure 19:
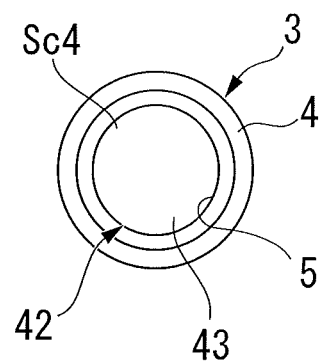
FIG. 19 is a view taken from the arrow J in FIG. 18.
Figure 20:
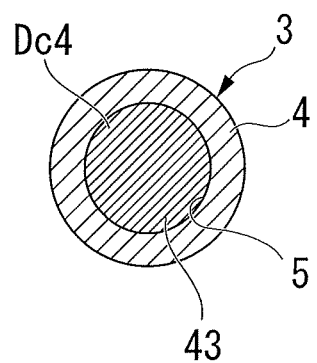
FIG. 20 is a view taken along the line I-I in FIG. 18.

Similar to the case of the first embodiment, the distal piece 42 is formed of a deformable material such as an elastic material, and the outer surface of the distal piece 42 is coated. For this reason, as shown in FIG. 18, the distal piece 42 can be deformed and accommodated in the lumen 5. As shown in FIG. 19, a projected area Sc4 in the axial direction becomes substantially equal to the cross-sectional area S11 of the lumen 5. Also, as shown in FIG. 20, a cross-sectional area Dc4 at the maximum width portion becomes substantially equal to the cross-sectional area S11 of the lumen 5.

The procedure of ERCP using the treatment device 41 is substantially the same as that of the first embodiment. The insertion section 3 is inserted into the papilla DN in a smooth manner while preventing the distal end portion from damaging or thrusting into mucous membranes since the distal piece 42 allows the distal end portion to form a generally rounded shape. When an operator pulls the wire 6 in order to pull out the wire 6, the piece body 43 is elastically deformed so that the piece body 43 is pulled into and passed through the lumen 5, whereby the wire 6 is pulled out toward the operator side.

In this embodiment, the distal piece 42 is configured to have a broad, large-curvature curved surface shape that distributes concentration of pressure acting on tissues, and the width d2 in the vertical direction of the piece body 43 is set larger than the lumen diameter, thereby alleviating or preventing damage or thrusting to mucous membranes. With such a configuration, it is possible to achieve the same advantages as the first embodiment. In addition, by configuring the width d1 in the horizontal direction of the piece body 43 so as to be smaller than the lumen diameter, it is possible to decrease the extent of deformation in the piece body 43 when pulled into the lumen 5. Therefore, it is possible to decrease the amount of force required for the pulling, and thus the usability of the device is improved. In addition, it is possible to decrease the load applied to the elastic material at the time of deformation of the piece body 43, and thus the durability of the device is improved.

Third Embodiment

Figure 21:
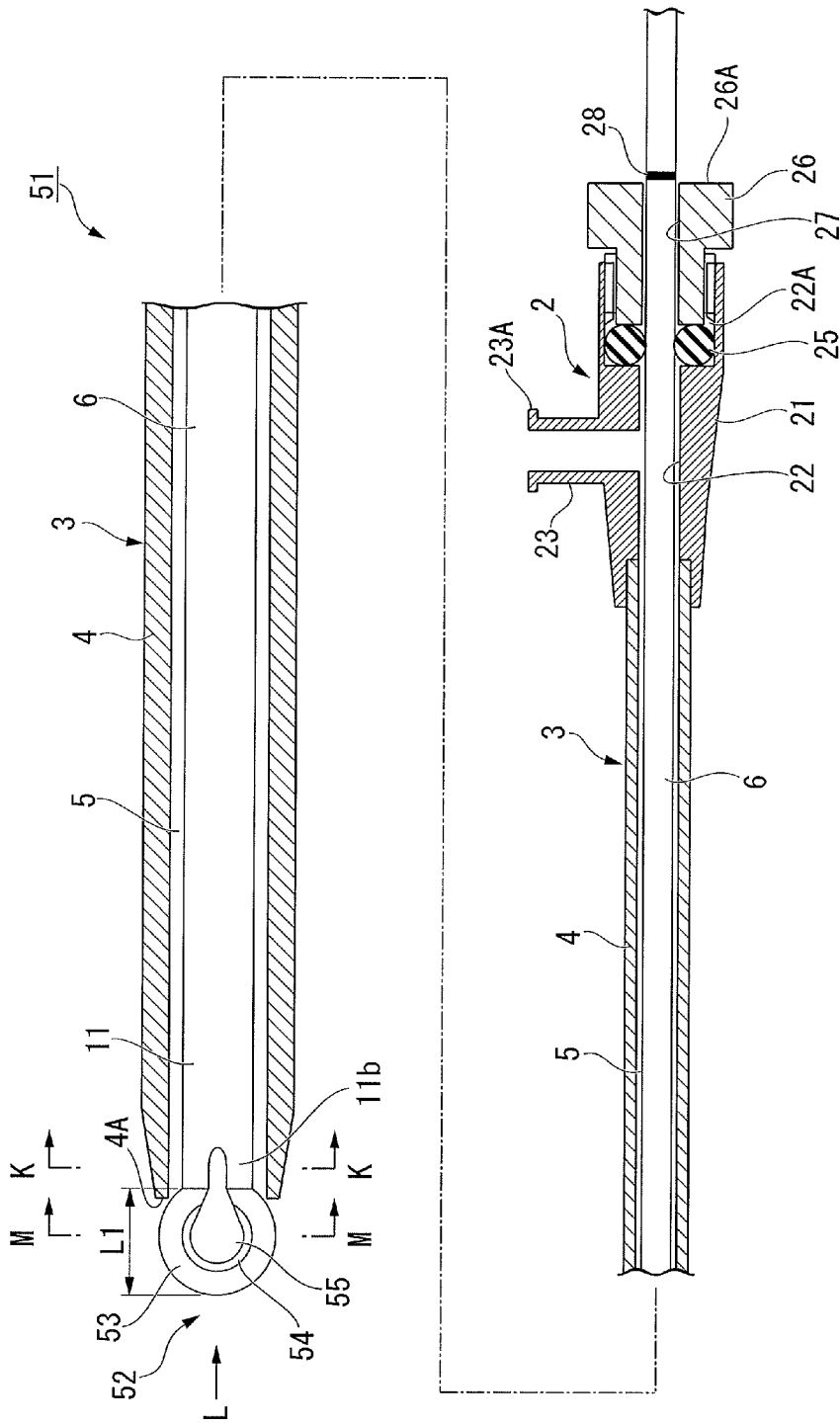
FIG. 21 is a cross-sectional view of a treatment device in which a slit is formed in a distal piece.

As shown in FIG. 21, in a treatment device 51, the distal piece attached to the distal end of the wire 6 has a shape different from that of the above-described embodiments.

A distal piece 52 is provided with a piece body 53 configured to protrude out from the distal end surface 4A of the catheter 4. The piece body 53 is formed of a deformable member such as an elastic member having a broad, large-curvature curved surface shape that distributes concentration of pressure acting on tissues, causing the distal end portion of the insertion section 3 to form a generally rounded shape. The piece body 53 has a pair of flat side surfaces 54. The side surfaces 54 are parallel to each other on both lateral portions of a spherical body, and a slit 55 is formed across the side surfaces 54 so as to penetrate through the piece body 53.

Figure 22:
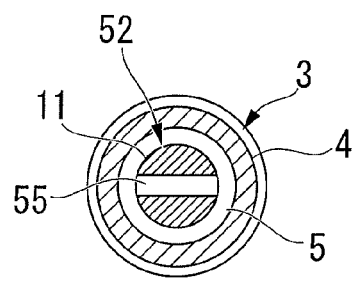
FIG. 22 is a cross-sectional view taken along the line K-K in FIG. 21.
Figure 23:
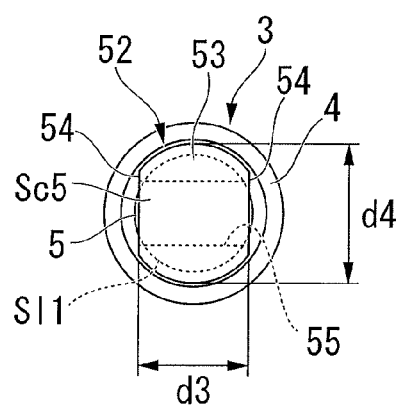
FIG. 23 is a view taken from the arrow L in FIG. 21.
Figure 24:
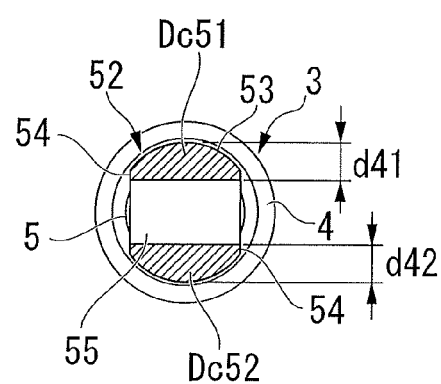
FIG. 24 is a cross-sectional view taken along the line M-M in FIG. 22.

As shown in FIGS. 21 and 22, a portion of the slit 55 extends to the base portion 11 and forms a proximal end portion 11b. As shown in FIG. 23, a width d3 of the piece body 53 in the horizontal direction parallel to the slit 55 is set smaller than the diameter of the lumen 5. A width d4 of the piece body 53 in the vertical direction perpendicular to both the horizontal direction and the axial direction is set larger than the diameter of the lumen 5 and smaller than the outer diameter of the catheter 4. A projected area Sc5 in the axial direction of the distal piece 52 when disposed outside the lumen 5 is set larger than the cross-sectional area S11 of the lumen 5. As shown in FIG. 24, the total area of a cross-sectional areas Dc51 and Dc52 of the distal piece 52 at a portion having the maximum width d4 in the vertical direction is set smaller than the cross-sectional area S11 of the lumen 5. In addition, to broaden the curved surface shape of the distal end of the piece body 53, the shape of each of the cross-sectional areas Dc51 and Dc52 is configured such that the width d3 in the horizontal direction is set larger than both respective widths d41 and d42 in the vertical direction of the cross-sectional areas Dc51 and Dc52 and that the cross-sectional areas Dc51 and Dc52 are in a substantially semi-circular shape.

Figure 25:
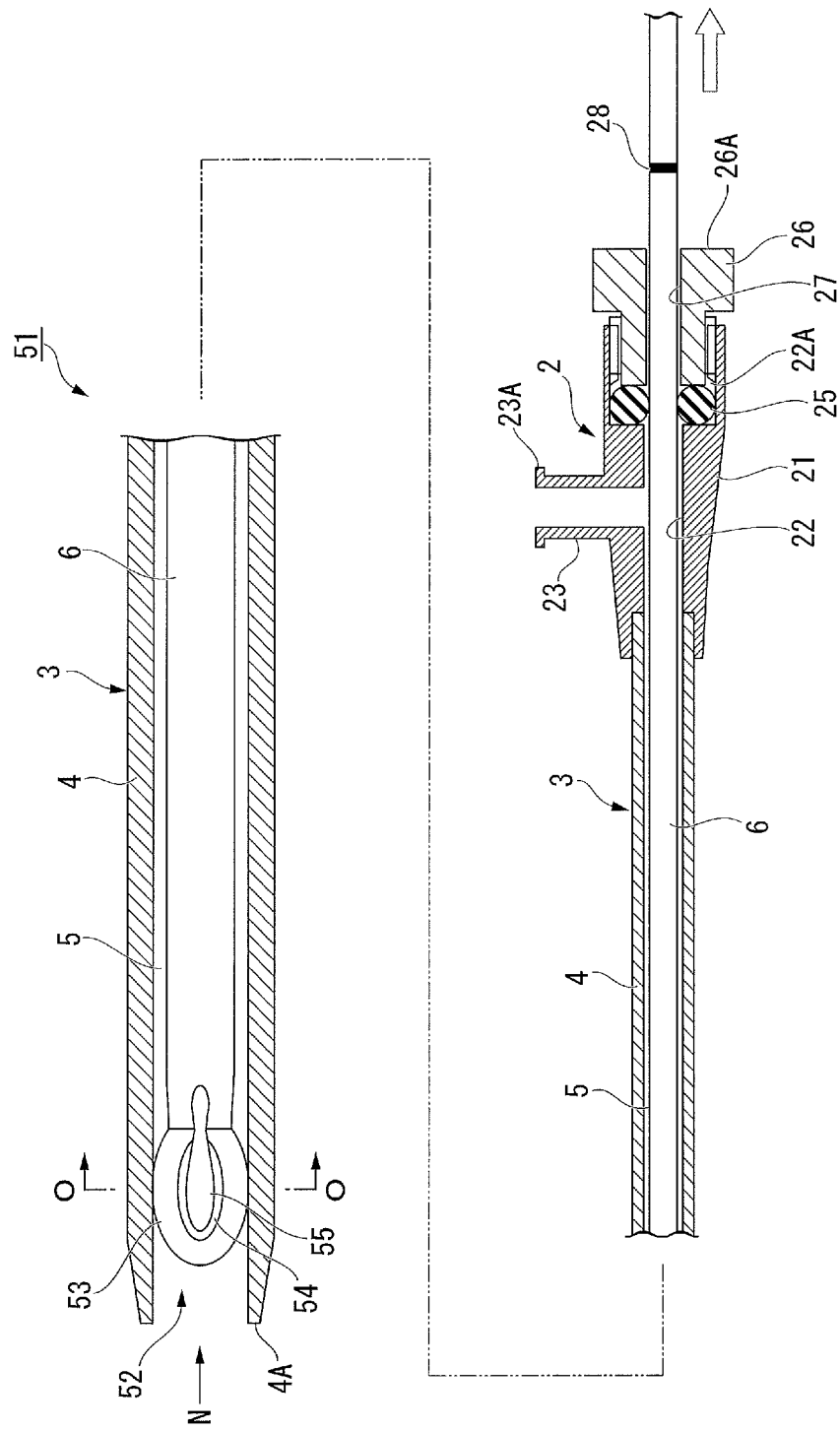
FIG. 25 is a view showing the case in which a distal piece is housed in a lumen.
Figure 26:
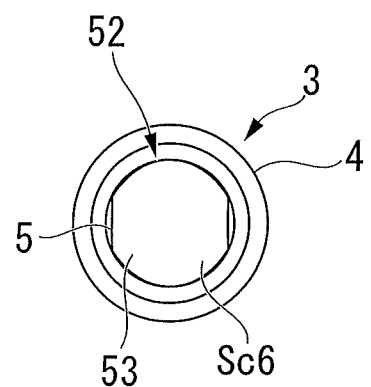
FIG. 26 is a view taken from the arrow N in FIG. 25.
Figure 27:
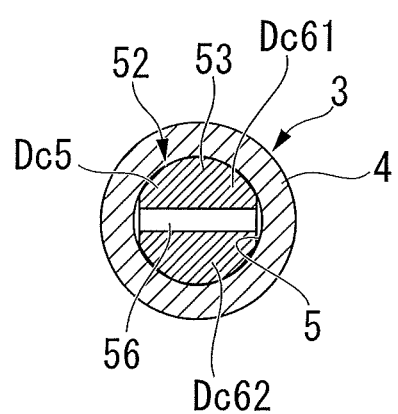
FIG. 27 is a view taken along the line O-O in FIG. 25.

As shown in FIGS. 25 and 26, in a state in which the distal piece 52 is pulled into the lumen 5, the projected area Sc6 of the distal piece 52 is set smaller than or equal to the cross-sectional area S11 of the lumen 5. FIG. 27 is a cross-sectional view taken at a position corresponding to FIG. 24: i.e., the position corresponding to the maximum width portion is shown. The width of the slit 55 is narrowed, so that the solid core portions come closer to each other. The total area of the cross-sectional areas Dcb1 and Dc62 becomes smaller than or equal to the cross-sectional area S11 of the lumen 5.

The cross-sectional area at the proximal end portion 11b disposed at the right rear side of the piece body 53 becomes smallest in the base portion 11.

The distal piece 52 is formed of a deformable material such as an elastic material. Since the piece body 53 is likely to be deformed by the slit 55, the elastic material can be used may be a material having a lower elasticity than rubber, such as polypropylene, polyethylene, polyurethane, polyamide, fluorine-contained resin, PEEK (polyether ether ketone), or PET (polyethylene terephthalate). The same material as the first embodiment may be used. Another slit may be formed in the vertical direction to cross the slit 55 so that there are slits in two directions, or additional slits may be formed to cross each other in several directions.

The procedure of ERCP using the treatment device 51 is substantially the same as that of the first embodiment. When an operator pulls out the wire 6, the piece body 53 is elastically deformed. The portion of the piece body 53 making first contact with the distal end surface 4A of the catheter 4 is deformed in a manner to decrease the width of the slit 55 and decrease the exterior shape of the piece body 53, and in response to this, the piece body 53 is pulled into the lumen 5.

In this embodiment, it is possible to achieve the same advantages as the first embodiment. Furthermore, since the slit 55 provides the same advantage as obtainable from the structure in which the distal end of the piece body 53 operates in a hinge manner, it becomes easy to change the size of the piece body 53 in the diameter direction. In addition, it is possible to decrease the amount of force required for pulling in the piece body 53, and thus the usability of the device is improved. Alternatively, it is possible to decrease the load applied to the elastic material at the time of deformation of the piece body 53, and thus the durability of the device is improved.

Since the cross-sectional area at the proximal end portion 11*b* disposed at the right rear side of the piece body 53 is smallest in the base portion 11, the piece body 53 is made easy to bend about the proximal end portion 11*b*. For this reason, the wire can be more easily curved in a manner to adopt the shape of the bile duct BD.

Alternatively, a slit may be provided to the piece body 12 of the first embodiment. In this case, the position or size of the slit is the same as that of the slit 55 provided to the piece body 53.

Fourth Embodiment

Figure 28:
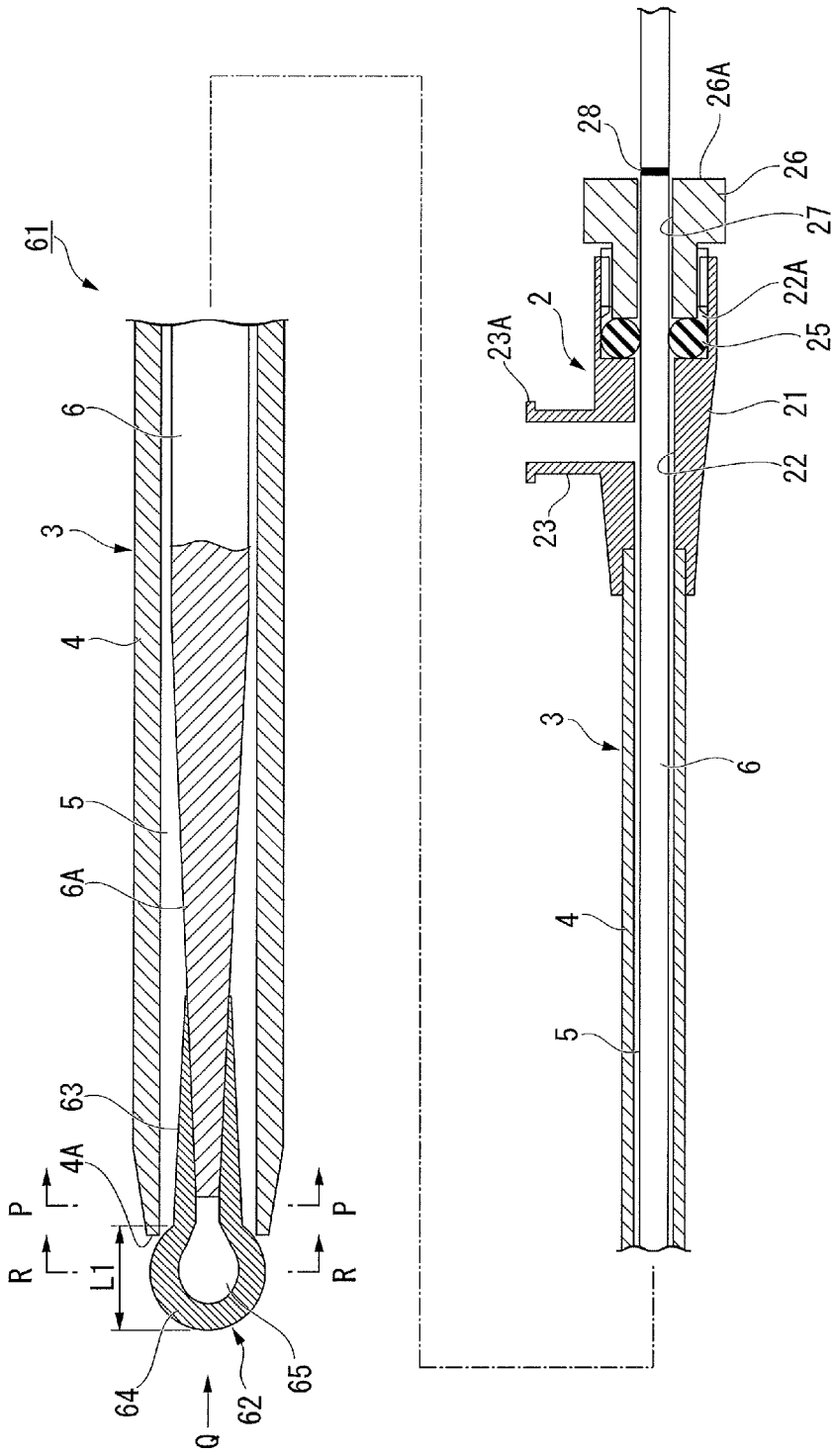
FIG. 28 is a sectional view of a treatment device with a hollow distal piece.

As shown in FIG. 28, in a treatment device 61, the distal piece attached to the distal end of the wire 6 has a shape different from that of the above-described embodiments.

Figure 29:
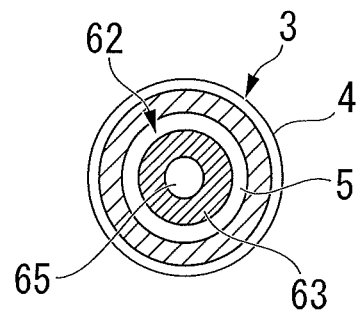
FIG. 29 is a sectional view taken along the line P-P in FIG. 28.
Figure 30:
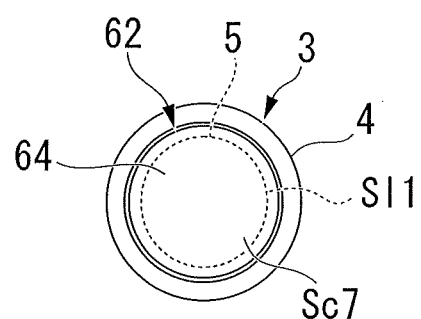
FIG. 30 is a view taken from the arrow Q in FIG. 28.
Figure 31:
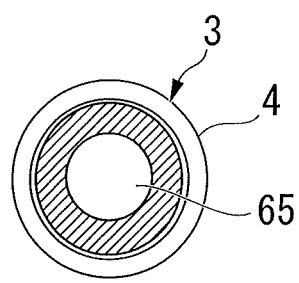
FIG. 31 is a cross-sectional view taken along the line R-R in FIG. 28.

As shown in FIGS. 28 and 29, a distal piece 62 is provided with a piece body 64 formed of an elastic material and having a broad, large-curvature curved surface shape that distributes concentration of pressure acting on tissues. The piece body 64 has a hollow shape in which a void 65 is formed extending to a proximal end portion 63 that is fitted to the wire 6. For this reason, as shown in FIG. 30, a projected area Sc7 in the axial direction of the piece body 64 is greater than the cross-sectional area S11 of the lumen 5, however, as shown in FIG. 31, a cross-sectional area Dc7 at a maximum diameter portion of the piece body 64 is smaller than the cross-sectional area S11 of the lumen 5. Other shapes or materials of the piece body 64 are the same as those of the first or third embodiment.

Figure 32:
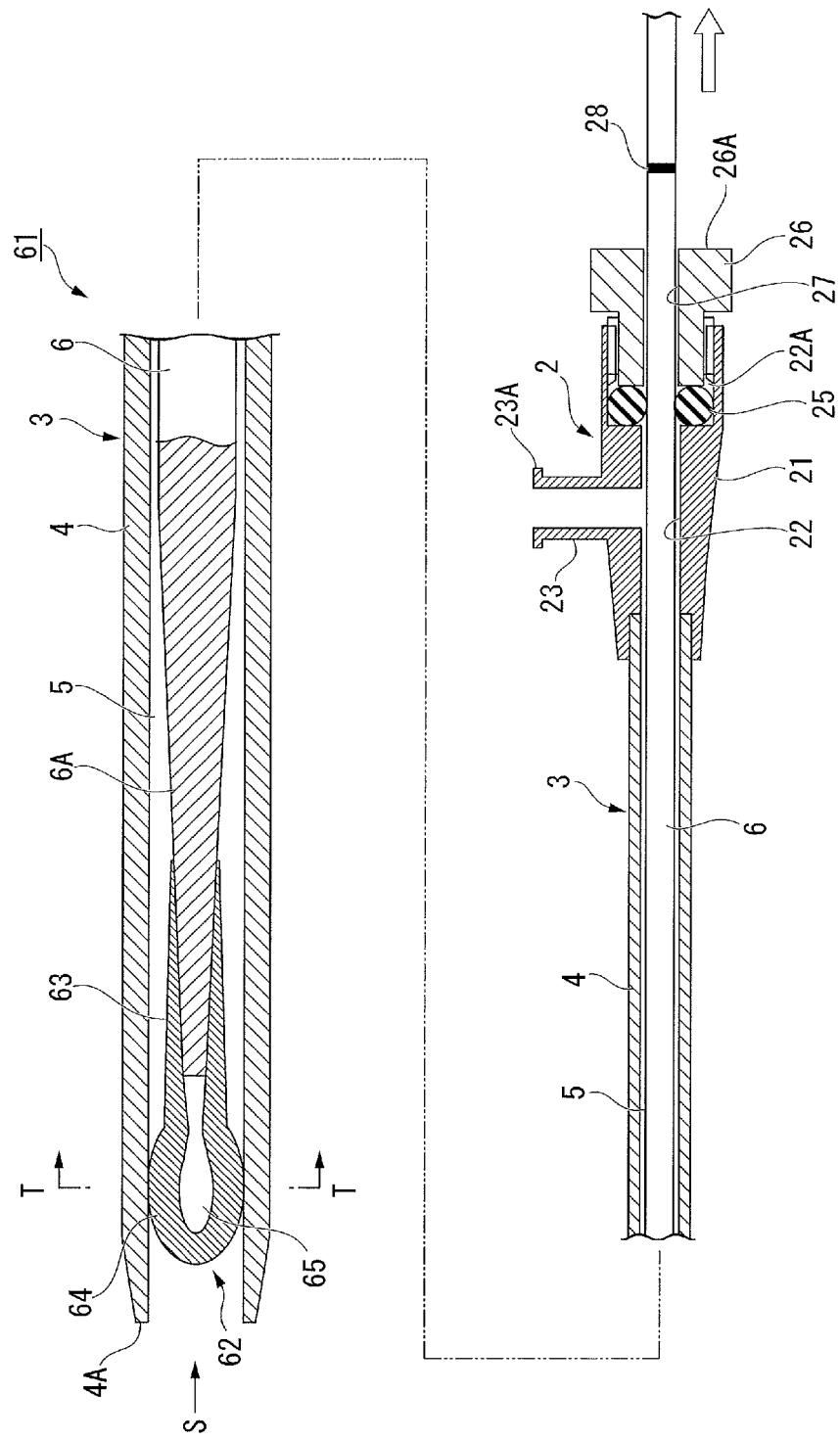
FIG. 32 is a view showing the case in which a distal piece is housed in a lumen.
Figure 33:
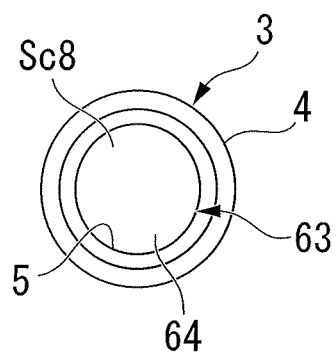
FIG. 33 is a view taken from the arrow S in FIG. 32.
Figure 34:
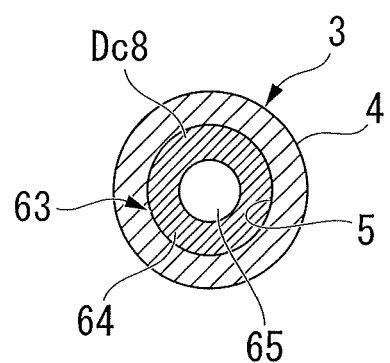
FIG. 34 is a view taken along the line T-T in FIG. 32.

As shown in FIG. 32, when the piece body 64 is pulled into the lumen 5, the piece body 64 is squeezed to deform the void 65 in the distal piece 62 in a long and thin manner. As shown in FIGS. 33 and 34, a projected area Sc8 in the axial direction and a cross-sectional area Dc8 at the maximum width portion become smaller than or equal to the cross-sectional area S11 of the lumen 5.

In this embodiment, since the void 65 is formed in the distal piece 62, the piece body 64 can be easily deformed and pulled into the lumen 5 with a small force. In addition, the load applied to the distal piece 62 can be decreased, and thus the durability of the device can be improved. Other advantages of this embodiment are the same as those of the first embodiment.

The distal piece 42 of the second embodiment may be formed in a hollow shape.

Fifth Embodiment

Figure 35:
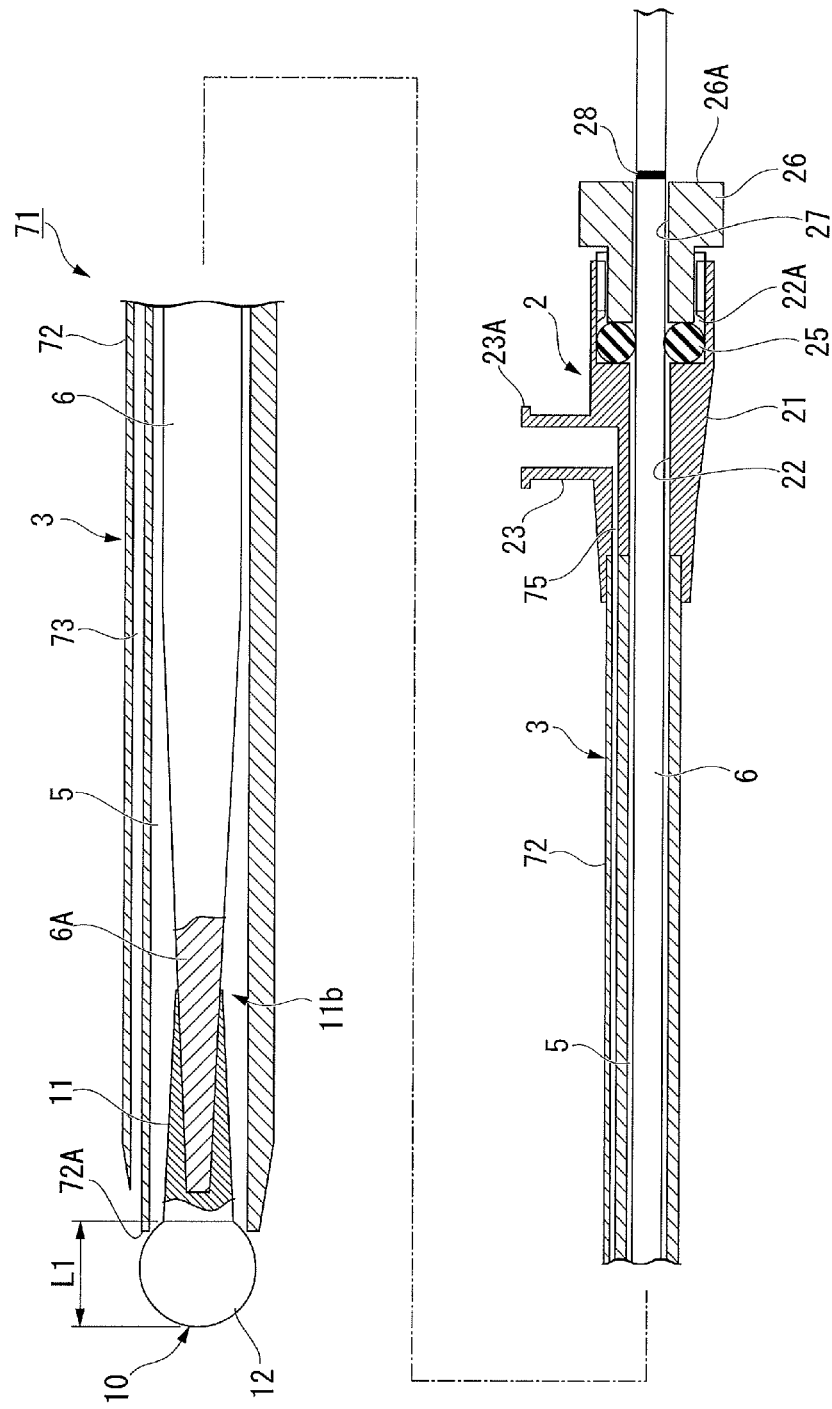
FIG. 35 is a cross-sectional view of a multi-lumen treatment device.

As shown in FIG. 35, the insertion section 3 of a treatment device 71 is provided with a multi-lumen type catheter 72.

The catheter 72 includes a first lumen, the guidewire lumen 5 for passing the wire 6, and a second lumen, a liquid supply lumen 73 disposed in parallel to the guidewire lumen 5. A distal opening of the liquid supply lumen 73 is disposed at the inclined portion in a tapered shape close to a distal end surface 72A of the catheter 72. A proximal end of the liquid supply lumen 73 is communicated with a liquid supply port via a communication hole 75 formed in the operation main body 21. The liquid supply port 23 is not communicated with the guidewire lumen 5.

The procedure of inserting the treatment device 71 into the bile duct BD through the papilla DN is the same as that of the above-described embodiments. At the time of imaging, a contrast agent is supplied from a syringe to the liquid supply lumen 73 via the liquid supply port 23 and the communication hole 75 and then supplied to the bile duct BD from the distal opening of the liquid supply lumen 73.

In this embodiment, since the catheter 72 is configured as a multi-lumen type catheter, even when the distal piece 10 blocks the distal opening of the guidewire lumen 5, it is possible to allow the contrast agent to be ejected from the distal end of the catheter 72. The distal piece 10 provides the same advantages as in the case of the first embodiment. Alternatively, the distal piece may also be the one used in any one of the second to fourth embodiments.

Sixth Embodiment

Figure 36:
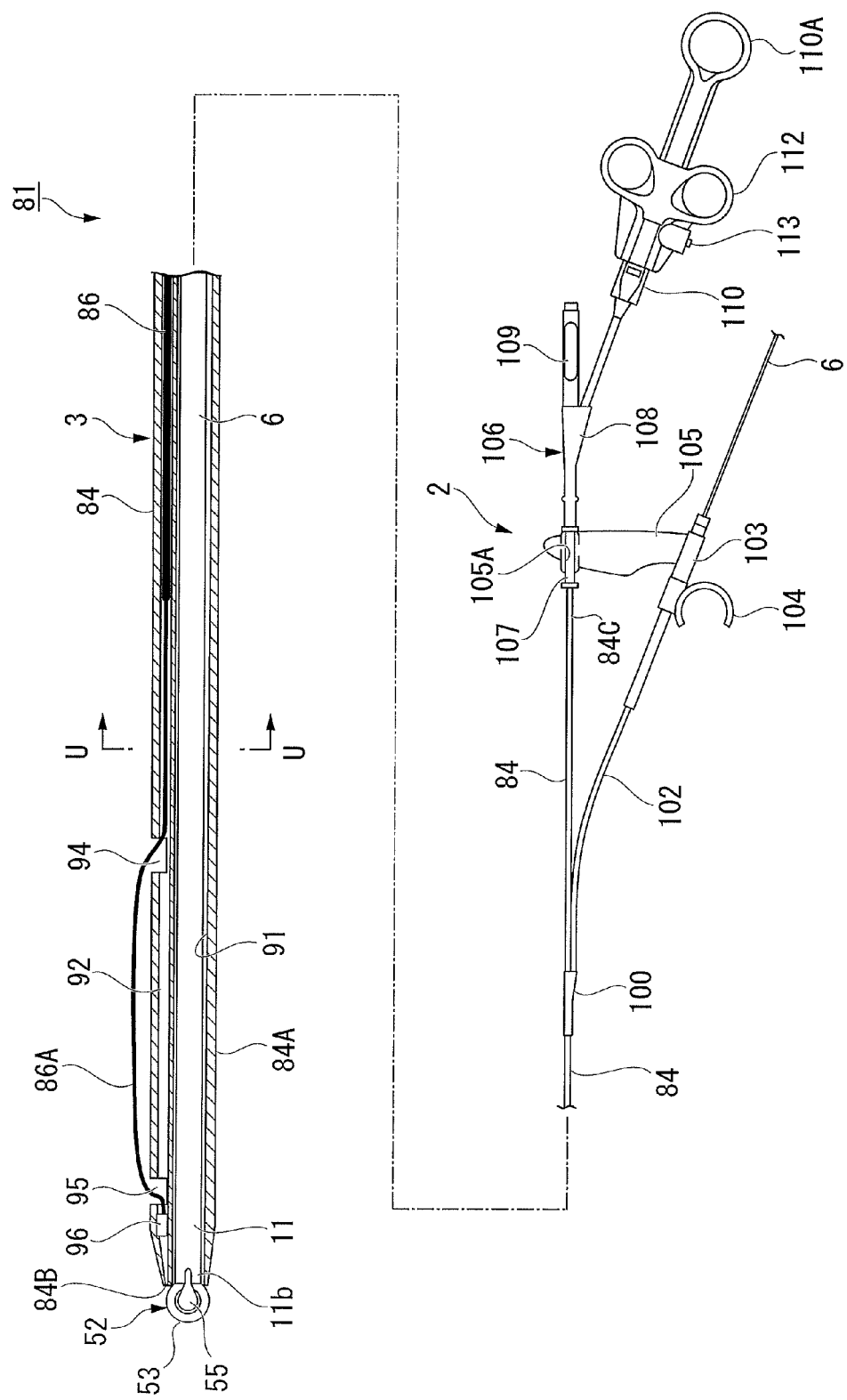
FIG. 36 is a cross-sectional view of a papillotome as an example of a treatment device, in which an incision knife portion is provided using a multi-lumen sheath.

As shown in FIG. 36, the treatment device of this embodiment is a papillotome 81 that can incise the papilla DN.

The papillotome 81 has the flexible insertion section 3 extending in a longitudinal direction from the operation section 2 with which an operator operates the papillotome 81. The insertion section 3 has a multi-lumen type catheter 84. A conductive wire 86 which is used for incision is drawn out on a lateral portion on the distal end side of the catheter 84.

Figure 37:
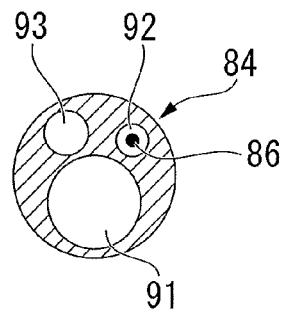
FIG. 37 is a cross-sectional view taken along the line U-U in FIG. 36.

As shown in FIG. 37, the catheter 84 has three lumens 91, 92, and 93 that are substantially parallel to each other and extend in the longitudinal direction.

A guidewire lumen 91 as the first lumen has the largest diameter among the three lumens and is opened to a distal end surface 84B of the catheter 84. The wire 6 can be freely advanced and retracted through the guidewire lumen 91. The distal piece 52 is fitted to the wire 6. The material and shape of the distal piece 52 and the size of the guidewire lumen 91 are the same as those of the third embodiment. In addition, guidewires other than the wire 6 may be inserted through the guidewire lumen 91.

A knife lumen 92 as the second lumen has the smallest diameter among the three lumens, and the distal end thereof is sealed. Two holes 94 and 95 are formed in the distal end of the knife lumen 92 in this order in the longitudinal direction away from the distal end, and the holes are opened to a lateral portion of the catheter 84. The conductive wire 86 is passed through the knife lumen 92. The conductive wire 86 is drawn out from the hole 94 formed in a lateral portion of the distal end surface 84A of the catheter 84 to be exposed to the outside of the catheter 84 and is inserted into the knife lumen 92 through the hole 95 formed close to the distal end. The portion that is drawn out on the outer periphery of the catheter 84 to be exposed to the outside serves as a knife portion that is used for treatment (hereinafter the portion will be referred to as an incision knife portion 86A). The distal end of the conductive wire 86 is fixed to the catheter 84 at a piece 96 that is buried in the knife lumen 92. When it is desired to bend the distal end portion 84A of the catheter 84 in a free curve shape, the distal end portion 84A may be provided with an ability to be bent in the direction for shortening the linear distance between the two holes 94 and 15.

A liquid supply lumen 93 as the third lumen has the second largest diameter among the three lumens, and the distal end thereof is opened. The liquid supply lumen 93 is used for supply of liquid such as a contrast agent.

The operation section 2 shown in FIG. 36 is provided with a first bifurcated portion 100 that communicates a tube 102 to the guidewire lumen 91 in the catheter 84. The tube 102 is flexible and is connected to an inserting section 103 at its end. The inserting section 103 has an opening so that the wire 6 can be inserted through the opening. A ring 104 is formed on a lateral portion of the inserting section 103. The ring 104 has a substantially C-shape that is opened at the distal end side. When the ring 104 is fitted to the endoscope, the operation section 2 can be fixed to the endoscope. A connecting portion 105 is integrally formed with the lateral portion of the inserting section 103 substantially opposite the disposition position of the ring 104. A concave portion 105A is formed in the distal end of the connection portion 105.

The operation section 2 is provided with an operation main body 106 that is fixed to an end portion 84C of the proximal end portion of the catheter 84 extending over the first bifurcated portion 100. The operation main body 106 has a lock portion 107 on its distal end. The lock portion 107 is detachably fitted to the concave portion 105A of the connecting portion 105. The operation main body 106 is bifurcated at a second bifurcated portion 108 from the lock portion 107 into a first operation unit 109 and a second operation unit 110. The first operation unit 109 is disposed substantially concentric to the catheter 84 and is communicated to the liquid supply lumen 93, and a syringe can be detachably fitted to its end. The second operation unit 110 is disposed inclined with respect to the first operation unit 109, and a slider 112 can freely advance and retract. A terminal 113 connectable to an external high-frequency power supply is installed in the slider 112 and is electrically connected to the conductive wire 86 that is fixed to the slider 112.

Next, the procedure using the papillotome 81 will be described.

Figure 38:
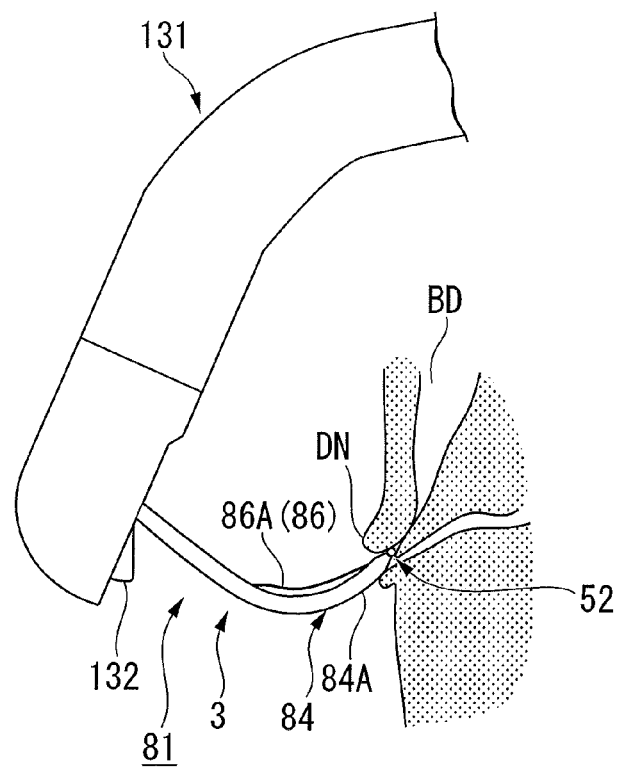
FIG. 38 is a view showing the case in which a distal end of a papillotome is inserted into a papilla.

While taking images of the interior of the body using an observation device installed in the endoscope, the distal end of the endoscope is advanced in the vicinity of a papilla of a treatment target. The papillotome 81 is inserted through a forceps plug of the endoscope into an instrument channel, and the distal end portion 84A of the catheter 84 is protruded from the endoscope. As shown in FIG. 38, the papillotome 81 is protruded out in the lateral direction by a forceps elevator 132 provided at the distal end of an endoscope 131. The distal edge of the catheter 84 is inserted through the papilla DN into the bile duct BD by the pre-curved shape of the distal end portion 84A. The distal end portion 84A of the catheter 84 can be inserted in a smooth manner while preventing the distal piece 52 from thrusting into the mucous membrane. A contrast agent is injected into the liquid supply lumen 93 from the syringe fitted to the first operation unit 109. The contrast agent is injected into the bile duct BD through the liquid supply lumen 93.

Figure 39:
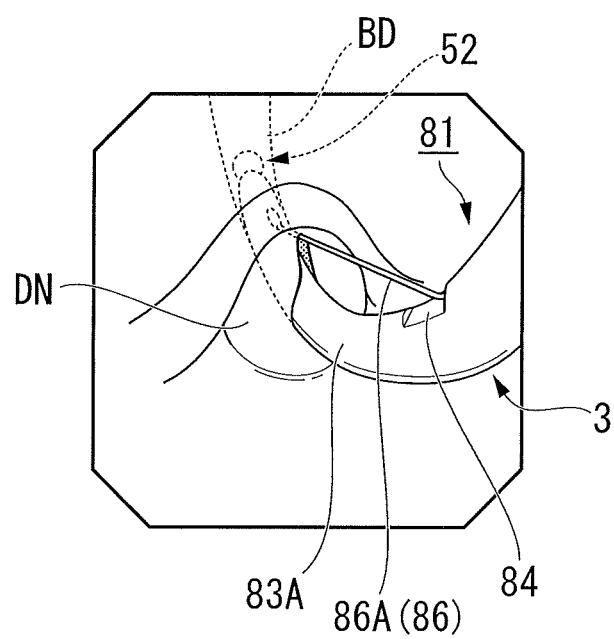
FIG. 39 shows an endoscopic image of an incised papilla

When an operator hooks his or her finger on a slider 112 and a ring 110A on the proximal end of the second operation unit 110 so as to retract the slider 112, the conductive wire 86 is pulled. Since the distal end of the conductive wire 86 is fixed to the distal end portion 84A of the catheter 84, the distal end portion 84A of the catheter 84 is curved. Depending on the requirements, only the wire 6 may be pushed further into the bile duct BD so that the distal end portion 84A is curved after the catheter 84 is stabilized. Since the incision knife portion 86A of the conductive wire 86 exposed to the outside from the catheter 84 is hung in an arch-like shape, the forceps elevator 132 is operated to oscillate the catheter 84 while flowing a high-frequency current from the high-frequency power supply to the conductive wire 86 via the terminal 113 on the slider 112 of the second operation unit 110. By the high-frequency current supplied to the tissue of the papilla DN making contact with the incision knife portion 86A and the tensile pressure of the incision knife portion 86A, the papilla DN is incised as shown in FIG. 39. When the papilla DN is sufficiently incised, the electrification of the high-frequency current is stopped. FIG. 39 shows an endoscopic image taken by the observation device disposed at the distal end of the endoscope 131.

When the incision of the papilla DN is completed, the slider 112 of the second operation unit 110 is restored to its normal position. Then, the catheter 84 is advanced into the bile duct BD through the papilla DN.

When the treatment is completed, the papillotome 81 is pulled out from the bile duct BD to retract the endoscope out of the body. When the treatment is continued using other treatment tools, the catheter 84 is advanced into the bile duct BD and the wire 6 is pulled out from the guidewire lumen 91. The distal piece 52 is pulled into the guidewire lumen 91 and drawn out of the inserting section 103 while being elastically deformed. Then, another guidewire is inserted through the inserting section 103 and introduced into the bile duct BD. Thereafter, the papillotome 81 is pulled out of the body while the guidewire is indwelled. Another treatment tool is introduced into the bile duct along the guidewire in order to perform a necessary treatment. Alternatively, only the papillotome 81 may be pulled out while the wire 6 is indwelled so that another treatment tool is inserted along the wire 6 in order to perform the treatment. When the treatment is completed, the treatment tool, the guidewire and the endoscope are retracted.

In this embodiment, since the incision of the papilla and fluoroscopy can be performed with a single treatment device, it is possible to obviate the necessity of changing to another device. Since the orientation of the distal end of the catheter 4 can be controlled by an operator's handle operation, it is possible to insert the papillotome 81 in a more reliable manner. The distal piece 52 provides the same advantages as in the case of the above-described embodiments. Alternatively, the distal piece may also be the one used in any one of the first, second and fourth embodiments.

Seventh Embodiment

Figure 40:
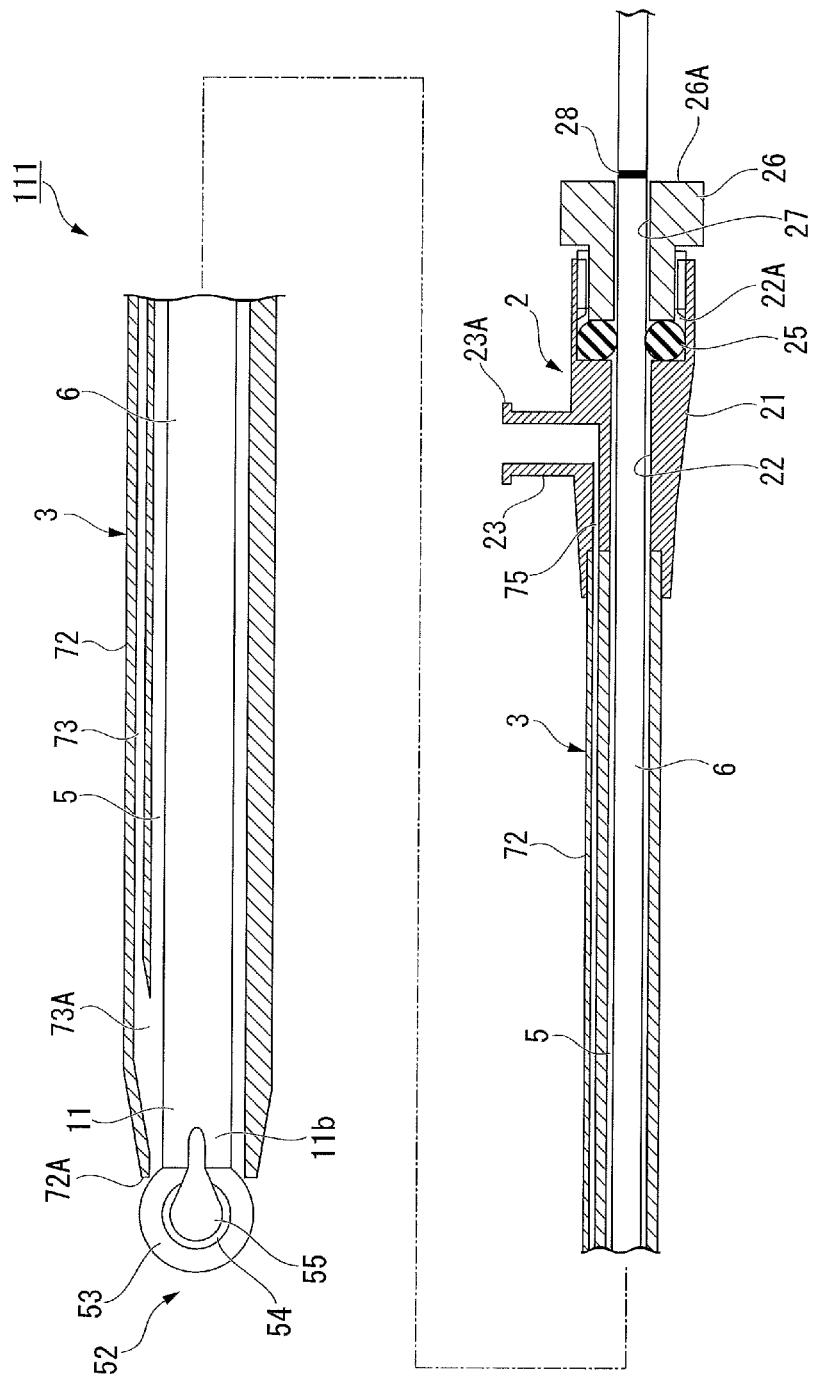
FIG. 40 is a cross-sectional view of a multi-lumen treatment device.

As shown in FIG. 40, the insertion section 3 of a treatment device 111 is provided with a multi-lumen type catheter 112.

The catheter 112 includes a first lumen which is the guidewire lumen 5 for passing the wire 6, and a second lumen which is the liquid supply lumen 73 disposed in parallel to the guidewire lumen 5. The distal end of the guidewire lumen 5 is opened to a distal end surface 72A of the catheter 72. The distal opening 73A of the liquid supply lumen 73 is not opened to the distal end surface 72A of the catheter 72 but opened to the vicinity of the distal end surface 72A disposed closer to the proximal end than the distal opening of the guidewire lumen 5. The distal opening 73A is communicated to the outside via the guidewire lumen 5.

A slit 55 is formed in the distal piece 52 disposed at the distal end of the wire 6.

The procedure of inserting the treatment device 111 into the bile duct BD through the papilla DN is the same as that of the above-described embodiments. At the time of imaging the bile duct BD, a contrast agent is injected from a syringe into the liquid supply port 23. The contrast agent is supplied to the liquid supply lumen 72 through the communication hole 75. The contrast agent is introduced into the guidewire lumen 5 from the distal opening 73A of the liquid supply lumen 73. Since the distal opening 73A is disposed in the vicinity of the distal end surface 72A of the catheter 72, the contrast agent is injected into the bile duct BD through the gap between the guidewire lumen 5, the wire 6, and the distal piece 52. Even when the distal piece 52 is in proximity to or in close contact with the distal opening of the guidewire lumen 5, the contrast agent is injected into the bile duct BD through the slit 55 formed in the distal piece 52 and extending to the proximal end portion 11.

In this embodiment, since the distal opening 73A of the liquid supply lumen 73 is not disposed at the distal end surface 72A of the catheter 72, the multi-lumen type catheter 72 can have a smoother tapered portion at its distal end. By virtue of the slit 55 of the distal piece 52, it is possible to allow the contrast agent to be ejected from the distal end of the catheter 72 in a reliable manner.

Since the distal piece 52 only needs to have a shape that allows elastic deformation and enables the liquid supply, the slit may be formed on the outer periphery of the distal piece 52. In addition, in the papillotome 81, the distal opening 73A of the liquid supply lumen 73 may be connected to the distal end portion of the guidewire lumen 5.

While preferred embodiments of the invention have been described and illustrated above, the invention is not limited thereto. Additions, omissions, substitutions, and other modifications can be made without departing from the scope of the invention. Accordingly, the invention is not to be considered as being limited by the foregoing description, and is only limited by the scope of the appended claims.

What is claimed is:

1. A treatment device, comprising:
a catheter having a lumen that is opened to a distal end of the catheter;
a wire passing through the lumen so that the wire is capable of being inserted into or retracted from the lumen; and
a piece disposed to extend distally past at a distal most end of the wire, the piece having a piece body in which a maximum width when the piece is protruded out from the distal end of the catheter is set larger than a diameter of the lumen, the piece body being formed of a deformable material such that it is elastically deformed when moved within the lumen and automatically restored to the maximum width when moved outside the lumen; wherein
the piece body includes a distal portion having a continuous, smooth, and curved surface shape, and the piece body further having a slit portion wherein a slit is formed, the slit portion being more proximal than the distal portion and more distal than the distal most end of the wire, the slit forming an unobstructed opening extending from a first side of the piece body to a second opposite side of the piece body, such that the slit allows the piece body to elastically deform when moved within the lumen, the piece body being formed of the deformable material that distributes concentration of pressure acting on tissues,
when the wire is pulled in toward the catheter, the piece body is pressed by an inner wall of the catheter such that the piece body is extended in an axial direction and an outer diameter of the piece body is reduced such that the piece body is capable of being housed in the lumen, and
when the wire is pushed such that the piece protrudes from the distal end of the catheter, the piece body is automatically restored to the curved surface shape.

2. The treatment device according to claim 1, wherein the catheter further comprises a liquid supply lumen, and a distal end of the liquid supply lumen is connected to the lumen.

3. The treatment device according to claim 1, wherein the catheter further comprises a knife lumen, and a conductive wire, which a portion of the conductive wire being exposed from an outer periphery on a distal end side of the catheter, passes through the knife lumen.

4. The treatment device according to claim 1, wherein the piece body has a hollow shape.

5. The treatment device according to claim 1, wherein a cross-sectional area at a portion of the piece body where the slit is formed in a direction perpendicular to the axial line of the lumen is smaller than a section area of the lumen.

6. The treatment device according to claim 5, wherein
a pair of flat side surfaces are formed on the surface of the piece body and parallel to each other,
the slit is formed across the side surfaces so as to penetrate through the piece body, and
a width of the piece body at which the slit is formed in the direction perpendicular to the axial line of the lumen is set smaller than the diameter of the lumen.

7. The treatment device according to claim 1, wherein the piece further includes a base portion which covers a periphery of a distal end portion of the wire.

8. The treatment device according to claim 1, wherein
a distal end portion of the wire is formed in a tapered shape, and
the distal end portion of the wire has a diameter smaller than an immediately adjacent portion of the wire.

9. The treatment device according to claim 1, wherein the catheter is a multi-lumen catheter having a guide wire lumen through which the wire is inserted and a liquid supply lumen, wherein
the guide wire lumen and the liquid supply lumen are disposed parallelly to each other, and
a distal opening of the liquid supply lumen is disposed at an inclined portion with a tapered shape, the inclined portion being at the distal end of the catheter.

* * * * *